(12) United States Patent
Hufton et al.

(10) Patent No.: US 7,898,407 B2
(45) Date of Patent: Mar. 1, 2011

(54) HAND HYGIENE COMPLIANCE SYSTEM

(75) Inventors: Graham Clive Hufton, Toronto (CA); Oleksandr Igorovich Levchenko, Mississauga (CA); Geoffrey Roy Fernie, Etobicoke (CA)

(73) Assignee: Toronto Rehabilitation Institute, Toronto ON (CA)

( * ) Notice: Subject to any disclaimer, the term of this patent is extended or adjusted under 35 U.S.C. 154(b) by 190 days.

(21) Appl. No.: 12/078,186

(22) Filed: Mar. 27, 2008

(65) Prior Publication Data
US 2008/0246599 A1    Oct. 9, 2008

Related U.S. Application Data

(60) Provisional application No. 60/920,779, filed on Mar. 30, 2007, provisional application No. 60/690,521, filed on Oct. 2, 2007.

(51) Int. Cl.
G08B 1/08 (2006.01)
G08B 23/00 (2006.01)
B67D 7/06 (2010.01)

(52) U.S. Cl. ............ 340/539.11; 340/539.12; 340/573.1; 340/286.07; 222/23

(58) Field of Classification Search ........... 340/539.11, 340/573.1
See application file for complete search history.

(56) References Cited

U.S. PATENT DOCUMENTS

| 692,089 | A | 1/1902 | Swisher |
|---|---|---|---|
| 2,059,135 | A | 1/1936 | Moe |
| 2,113,022 | A | 4/1938 | Hefti |
| 2,235,350 | A | 3/1941 | Violet |
| 2,975,719 | A | 3/1961 | Kaufman |
| 3,202,331 | A | 8/1965 | Robert |
| 3,273,752 | A | 9/1966 | Horeczky |
| 3,434,628 | A | 3/1969 | Ceraldi |
| 3,478,344 | A | 11/1969 | Schwitzgebel et al. |

(Continued)

FOREIGN PATENT DOCUMENTS

WO   WO 2006/119373   11/2006

(Continued)

OTHER PUBLICATIONS

Inuzaka and Hyodo, "Research on Healthcare Worker Behavior to Increase Hand Hygiene Compliance in a Japanese Hospital", Poster Abstracts: Infection Prevention and Control Programs, Publication No. 9-122, 34th Annual Education Conference & International Meeting, Jun. 24-28, 2007, San Jose, CA, p. 85.

(Continued)

Primary Examiner—Donnie L Crosland

(57) ABSTRACT

A system and method of encouraging compliance of hand hygiene in an environment where users move from zone to zone and are required to perform hand hygiene between the zones. Users carry a wearable zone sensor which detects zones, detects hand hygiene actions, logs time of changing zones, and hand hygiene actions. The wearable sensor can be integral with a wearable hand hygiene product dispenser and/or can operate in cooperation with a fixed dispenser configured to transmit hand hygiene actions to the wearable zone sensor. The wearable zone sensors are configured to be useable anonymously or to be associated with a user identifier, and to interface with a central computer via a docking station or communication interface to transfer data for later analysis.

30 Claims, 20 Drawing Sheets

U.S. PATENT DOCUMENTS

| | | |
|---|---|---|
| 3,480,787 A | 11/1969 | Johansen |
| 3,516,575 A | 6/1970 | Moffitt |
| 3,547,324 A | 12/1970 | Parks |
| 3,612,353 A | 10/1971 | Haase |
| 3,630,172 A | 12/1971 | Neumann et al. |
| 3,635,189 A | 1/1972 | Whittemore |
| 3,647,115 A | 3/1972 | McCann et al. |
| 3,650,435 A | 3/1972 | Kleefeld |
| 3,696,384 A | 10/1972 | Lester |
| 3,739,329 A | 6/1973 | Lester |
| 3,843,020 A | 10/1974 | Bardeau et al. |
| 3,843,032 A | 10/1974 | Moran et al. |
| 3,881,641 A | 5/1975 | Pliml, Jr. et al. |
| 3,967,478 A | 7/1976 | Guinn |
| 3,993,251 A | 11/1976 | Des Garets |
| 4,053,233 A | 10/1977 | Bien et al. |
| 4,058,237 A | 11/1977 | Luke |
| 4,087,675 A | 5/1978 | Sansonetti |
| 4,145,769 A | 3/1979 | MacFarlane et al. |
| 4,164,306 A | 8/1979 | Perrin |
| 4,175,704 A | 11/1979 | Cohen |
| 4,271,988 A | 6/1981 | Clausen |
| 4,275,385 A | 6/1981 | White |
| 4,349,133 A | 9/1982 | Christine |
| 4,381,022 A | 4/1983 | Medynski |
| 4,420,097 A | 12/1983 | Motsenbocker |
| 4,513,885 A | 4/1985 | Hogan |
| 4,515,294 A | 5/1985 | Udall |
| 4,550,676 A | 11/1985 | Francis |
| 4,564,127 A | 1/1986 | Garabedian et al. |
| 4,570,827 A | 2/1986 | Roggenburg, Jr. et al. |
| 4,573,612 A | 3/1986 | Maddison et al. |
| 4,582,227 A | 4/1986 | Kanfer |
| 4,603,794 A | 8/1986 | DeFord et al. |
| 4,606,085 A | 8/1986 | Davies |
| 4,615,476 A | 10/1986 | Hobbs et al. |
| 4,620,646 A | 11/1986 | Crapser |
| 4,634,022 A | 1/1987 | O'Halloran et al. |
| 4,635,689 A | 1/1987 | Graffin |
| 4,637,934 A | 1/1987 | White |
| 4,645,094 A | 2/1987 | Acklin et al. |
| 4,662,873 A | 5/1987 | Lash et al. |
| 4,667,854 A | 5/1987 | McDermott et al. |
| 4,673,109 A | 6/1987 | Cassia |
| 4,689,935 A | 9/1987 | Harding |
| 4,703,871 A | 11/1987 | Broker |
| 4,709,330 A | 11/1987 | Yokoi et al. |
| 4,711,373 A | 12/1987 | Christine |
| 4,722,372 A | 2/1988 | Hoffman et al. |
| 4,736,876 A | 4/1988 | Kriss |
| 4,741,461 A | 5/1988 | Williamson et al. |
| 4,768,688 A | 9/1988 | Harrigan |
| 4,793,517 A | 12/1988 | Washut |
| 4,886,192 A | 12/1989 | Cassia |
| 4,896,144 A | 1/1990 | Bogstad |
| 4,938,384 A | 7/1990 | Pilolla et al. |
| 4,944,429 A | 7/1990 | Bishop et al. |
| 4,946,070 A | 8/1990 | Albert et al. |
| 4,946,072 A | 8/1990 | Albert et al. |
| 4,952,928 A | 8/1990 | Carroll et al. |
| 4,967,935 A | 11/1990 | Celest |
| 4,990,892 A | 2/1991 | Guest et al. |
| 5,016,172 A | 5/1991 | Dessertine |
| 5,016,781 A | 5/1991 | Ten Wolde |
| 5,018,646 A | 5/1991 | Billman et al. |
| D317,984 S | 7/1991 | Reynoso et al. |
| 5,031,258 A | 7/1991 | Shaw |
| 5,037,389 A | 8/1991 | Dooley |
| 5,046,648 A | 9/1991 | Herbstzuber |
| 5,072,935 A | 12/1991 | Mcwain |
| 5,088,624 A | 2/1992 | Hackett |
| 5,117,766 A | 6/1992 | Nechushtan et al. |
| 5,129,999 A | 7/1992 | Holland et al. |
| 5,148,949 A | 9/1992 | Luca |
| 5,154,318 A | 10/1992 | Lampard |
| 5,199,609 A | 4/1993 | Ash, Jr. |
| 5,202,666 A | 4/1993 | Knippscheer |
| 5,204,670 A | 4/1993 | Stinton |
| 5,215,227 A | 6/1993 | Farner |
| 5,248,066 A | 9/1993 | Olson et al. |
| 5,261,570 A | 11/1993 | Hippely et al. |
| 5,265,628 A | 11/1993 | Sage et al. |
| 5,265,772 A | 11/1993 | Bartasevich et al. |
| 5,284,133 A | 2/1994 | Burns et al. |
| 5,289,948 A | 3/1994 | Moss et al. |
| 5,307,953 A | 5/1994 | Regan |
| 5,341,993 A | 8/1994 | Haber et al. |
| 5,348,193 A | 9/1994 | Bruckner et al. |
| 5,363,842 A | 11/1994 | Mishelevich et al. |
| 5,370,267 A | 12/1994 | Schroeder |
| 5,387,993 A | 2/1995 | Heller et al. |
| 5,411,173 A | 5/1995 | Weinstein |
| 5,414,405 A | 5/1995 | Hogg et al. |
| 5,420,797 A | 5/1995 | Burns |
| 5,421,489 A | 6/1995 | Holzner, Sr. et al. |
| 5,429,301 A | 7/1995 | Franks |
| 5,443,236 A | 8/1995 | Bell et al. |
| 5,455,851 A | 10/1995 | Chaco et al. |
| 5,458,135 A | 10/1995 | Patton et al. |
| 5,464,125 A | 11/1995 | Daansen |
| 5,465,877 A | 11/1995 | Bell et al. |
| 5,484,085 A | 1/1996 | Bennett |
| RE35,187 E | 3/1996 | Gortz |
| 5,503,302 A | 4/1996 | Dejonge |
| 5,505,192 A | 4/1996 | Samiotes et al. |
| 5,509,578 A | 4/1996 | Livingstone |
| 5,537,992 A | 7/1996 | Bjoernstijerna et al. |
| 5,538,164 A | 7/1996 | Rivas |
| 5,566,869 A | 10/1996 | Katz |
| 5,582,323 A | 12/1996 | Kurtenbach |
| 5,608,643 A | 3/1997 | Wichter et al. |
| 5,610,589 A | 3/1997 | Evans et al. |
| 5,620,656 A | 4/1997 | Wensky et al. |
| 5,622,163 A | 4/1997 | Jewett et al. |
| 5,625,659 A | 4/1997 | Sears |
| 5,632,414 A | 5/1997 | Merriweather, Jr. |
| 5,669,529 A | 9/1997 | Levit |
| 5,670,945 A | 9/1997 | Applonie |
| 5,678,720 A | 10/1997 | Van Melle |
| 5,678,730 A | 10/1997 | Fabek et al. |
| 5,683,012 A | 11/1997 | Villaveces |
| 5,695,091 A | 12/1997 | Winnings et al. |
| 5,774,865 A | 6/1998 | Glynn |
| 5,793,653 A | 8/1998 | Segal |
| 5,798,714 A | 8/1998 | Nyfelt |
| 5,808,553 A | 9/1998 | Cunningham |
| 5,810,201 A | 9/1998 | Besse et al. |
| 5,812,059 A | 9/1998 | Shaw et al. |
| 5,815,467 A | 9/1998 | Deering |
| 5,824,407 A | 10/1998 | Hayashi et al. |
| 5,830,490 A | 11/1998 | Weinstein et al. |
| 5,836,482 A | 11/1998 | Ophardt et al. |
| 5,850,344 A | 12/1998 | Conkright |
| 5,860,437 A | 1/1999 | Fernie |
| 5,862,956 A | 1/1999 | Brandenburg et al. |
| 5,863,497 A | 1/1999 | Dirksing |
| 5,867,829 A | 2/1999 | Hegoas et al. |
| 5,870,015 A | 2/1999 | Hinkel |
| D408,988 S | 5/1999 | Barber et al. |
| 5,900,067 A | 5/1999 | Jones |
| 5,912,818 A | 6/1999 | Mcgrady et al. |
| 5,917,425 A | 6/1999 | Crimmins et al. |
| 5,924,601 A | 7/1999 | Chen |
| 5,927,548 A | 7/1999 | Villaveces |

| | | |
|---|---|---|
| 5,939,974 A | 8/1999 | Heagle et al. |
| 5,941,241 A | 8/1999 | Weinstein et al. |
| 5,944,227 A | 8/1999 | Schroeder et al. |
| 5,945,910 A | 8/1999 | Gorra |
| 5,952,924 A | 9/1999 | Evans et al. |
| 5,954,069 A | 9/1999 | Foster |
| 5,960,991 A | 10/1999 | Ophardt |
| 5,972,126 A | 10/1999 | Fernie |
| D416,417 S | 11/1999 | Ross et al. |
| 6,038,331 A | 3/2000 | Johnson |
| 6,065,639 A | 5/2000 | Maddox et al. |
| 6,125,482 A | 10/2000 | Foster |
| 6,131,773 A | 10/2000 | Wade et al. |
| 6,161,227 A | 12/2000 | Bargenquast |
| 6,236,317 B1 | 5/2001 | Cohen et al. |
| 6,236,953 B1 | 5/2001 | Segal |
| 6,278,372 B1 | 8/2001 | Velasco, Jr. et al. |
| 6,283,334 B1 | 9/2001 | Mahaffey et al. |
| 6,325,245 B1 | 12/2001 | Matthews |
| 6,375,038 B1 | 4/2002 | Daansen et al. |
| 6,386,390 B1 | 5/2002 | Tinker |
| 6,392,546 B1 | 5/2002 | Smith |
| 6,426,701 B1 | 7/2002 | Levy et al. |
| 6,467,651 B1 | 10/2002 | Muderlak et al. |
| 6,524,390 B1 | 2/2003 | Jones |
| 6,537,244 B2 | 3/2003 | Paukovits et al. |
| 6,564,999 B1 | 5/2003 | Saveliev et al. |
| 6,577,240 B2 | 6/2003 | Armstrong |
| 6,727,818 B1 | 4/2004 | Wildman et al. |
| 6,875,539 B2 | 4/2005 | Ophardt |
| 6,876,303 B2 | 4/2005 | Reeder et al. |
| 6,882,278 B2 | 4/2005 | Winings |
| 6,883,563 B2 | 4/2005 | Smith |
| 6,897,780 B2 | 5/2005 | Ulrich et al. |
| 6,937,150 B2 | 8/2005 | Medema et al. |
| 6,938,795 B2 | 9/2005 | Barton et al. |
| 6,970,574 B1 | 11/2005 | Johnson |
| D512,648 S | 12/2005 | Smith et al. |
| 6,975,231 B2 | 12/2005 | Lane et al. |
| 6,982,639 B2 | 1/2006 | Brackett et al. |
| 6,983,864 B1 | 1/2006 | Cagle |
| 6,990,391 B1 | 1/2006 | Cunha et al. |
| 7,015,816 B2 | 3/2006 | Wildman et al. |
| 7,070,067 B1 | 7/2006 | Buchanan et al. |
| 7,114,510 B2 | 10/2006 | Peters et al. |
| 7,135,011 B2 | 11/2006 | Powers et al. |
| 7,242,307 B1 | 7/2007 | LeBlond et al. |
| 7,271,728 B2 | 9/2007 | Taylor et al. |
| 7,286,057 B2 | 10/2007 | Bolling |
| 7,482,936 B2 | 1/2009 | Bolling |
| 7,605,704 B2 | 10/2009 | Munro et al. |
| 7,818,083 B2 | 10/2010 | Glenn et al. |
| 7,825,812 B2 | 11/2010 | Ogrin et al. |
| 7,855,651 B2 | 12/2010 | LeBlond et al. |
| 2002/0000449 A1 | 1/2002 | Armstrong |
| 2002/0135486 A1 | 9/2002 | Brohagen et al. |
| 2003/0019536 A1 | 1/2003 | Smith |
| 2003/0030562 A1 | 2/2003 | Lane et al. |
| 2003/0033669 A1 | 2/2003 | Fernie |
| 2004/0090333 A1 | 5/2004 | Wildman et al. |
| 2004/0138631 A1 | 7/2004 | Harper |
| 2004/0150527 A1 | 8/2004 | Harper et al. |
| 2004/0236470 A1 | 11/2004 | Dooley et al. |
| 2005/0248461 A1 | 11/2005 | Lane et al. |
| 2006/0013739 A1 | 1/2006 | Castillo et al. |
| 2006/0132316 A1 | 6/2006 | Wildman et al. |
| 2006/0240397 A1 | 10/2006 | Lynn et al. |
| 2006/0289567 A1 | 12/2006 | Shoham et al. |
| 2007/0008146 A1 | 1/2007 | Taylor et al. |
| 2007/0015552 A1 | 1/2007 | Bolling |
| 2007/0213877 A1 | 9/2007 | Hart et al. |
| 2007/0222554 A1 | 9/2007 | Hart |
| 2008/0001763 A1 | 1/2008 | Raja et al. |

FOREIGN PATENT DOCUMENTS

| | | |
|---|---|---|
| WO | WO/2008/119158 A1 | 10/2008 |
| WO | WO/2008/119158 | 9/2009 |
| WO | WO/2010/034125 A1 | 4/2010 |

OTHER PUBLICATIONS

Broughall et al., An automatic monitoring system for measuring handwashing frequency in hospital wards, Journal of Hospital Infection, 1984, p. 447, vol. 5, Elsevier, online.

Voss and Widmer, No Time for Handwashing, Infection Control and Hospital Epidemiology, 1997, p. 205, vol. 18, 3, ProQuest Nursing & Allied Health Source, online.

Xhale Innovations Inc., Hygreen: The Intelligent Hand Hygiene System, 2009, www.xhale.com/hygreen/index.asp, Xhale Innovations Inc., Florida, USA.

Harbor Medical, Inc., The Sprixx Hand Hygiene System, 2007, www.sprixx.com/shhsoverview.html, Harbor Medical, Inc., CA, USA.

Zhou et al, Activity analysis, summerization, and visualization . . . , IEEE Transactions on Circuits and Systems for Video Technology, 2008, pp. 1489-1498, v18.

Nguyen et al, Recognizing and monitoring high-level . . . IEEE Computer Society Conference on Computer Vision and Pattern Recognition, 2, 2003, 620-625.

Ohmura et al, B-pack: A bluetooth-based wearable sensing device for nursing activity recognition, 1st International Symposium, 2006, p. 6.

Naya et al, Workers' routine activity recognition using body movements and location information, Wearable Computers, 10th IEEE International Symposium, 2006 p. 105-108.

Minnen et al, Recognizing and discovering human actions from on-body sensor data, IEEE International Conference on Multimedia and Expo, 2005 p. 1545-1548.

Pirttikangas et al, Feature Selection and Activity Recognition from Wearable Sensors, Berlin: Springer-Verlag Berlin, 2006, pp. 516-527, vol. 4239.

Karantonis et al, Implementation of a real-time human movement classifier . . . , IEEE Transactions on Information Technology in Biomedicine, 2006 pp. 156-167, vol. 10.

Thies et al, Comparison of linear acceleration from three measurements systems during reach and grasp, Medical Engineering and Physics, Nov. 2007, p. 967-972, vol. 29.

Henmi et al, A biomechanical study of activities of daily living using neck and upper limbs . . . , Mod Rheumatol,Oct. 2006, pp. 289-293, vol. 16.

Bao and Intille, Activity recognition from user-annotated acceleration data, Berlion: Springer-Verlag Berlin, 2004, pp. 1-17, vol. 3001.

Ravi et al, Activity recognition from accelerometer data, Proceedings of the National Conference on Artificial Intelligence, 2005, (3) p. 1541-1546.

Lester et al, A practical approach to recognizing physical activities, Pervasive Computing, 2006, pp. 1-16, vol. 3968.

Nguyen et al, Unsupervised clustering of free-living human activities using ambulatory accelerometry, Conf Proc IEEE Eng Med Biol Soc 2007, pp. 4895-4898, vol. 1.

Lukowicz et al, Recognizing Workshop Activity using body worn microphones and accelerometers, Lecture Notes in Computer Science, 2004, pp. 18-32, vol. 3001/2004.

Duong et al, Activity recognition and abnormality detection with . . . ,Proceedings 2005 IEEE Computer Society Conference on Compute recognition, pp. 838-845, vol. 1, Jun. 2005.

Chen et al, Bathroom activity monitoring based on sound, Pervasive Computing. Third International Conference, 2005, pp. 47-61, vol. 3468.

Helmi et al, Human activity recognition using a fuzzy inference system, FUZZ-IEEE 2009. IEEE International Conference on Fuzzy Systems, Oct. 2, 2009, pp. 1897-1902.

Godfrey et al, Direct measurement of human movement by accelerometry, Medical Engineering and Physics,2008, pp. 1364-1386, vol. 30.

Moore et al, Comparing hand hygiene adherence rates for existing hand hygiene products . . . , Canadian Hospital Infection Control and Association, Annual Meeting, May 6-10, 2006.

Van De Mortel and Murgo, An examination of covert observation and solution audit tools . . . ,American journal of Infection Control, 2006, pp. 95-99, vol. 34(3).

Dubbert et al, Increasing ICU staff handwashing: effects of education and group feedback, Infect Control Hosp Epidemiol, 1990, p. 191-193, vol. 11.

Van De Mortel and Heyman, Performance feedback increases the incidence of handwashing by staff following patient contact in intensive care, Aust Crit Care, 1995, p. 8-13, vol. 8.

Pittet et al, Effectivness of a hospitasl-wide programme to improve compliance with hand hygiene, Lancet, 2005, pp. 1307-1312, vol. 356.

Tvedt and Bukholm, Alcohol-based hand disinfection: a more robust hand-hygiene method in an intensive care unit, J Hosp Infect, 2005, pp. 229-234, vol. 59.

Swoboda et al, Electronic monitoring and voice prompts improve hand hygiene and decrease nosocomial infections . . . , Crit Care Med, 2004, pp. 358-363, vol. 32.

Boyce, Hand Hygiene compliance, monitoring: current perspectives from the USA, Journal of Hospital Infections, 2008, pp. 2-7, vol. 70.

Kinsella et al, Electronic surveillance of wallmounted soap and alcohol gel dispensers in an intensive care unit, Journal of Hospital Infection, 2007, pp. 34-39, vol. 66.

Rosenthal et al, Reduction of nosocomical infection with improved hand hygiene in intensive care units . . . , Am J Infect Control, 2005, pp. 392-397, vol. 33 (7).

Creedon, Health care workers' hand decontamination practices: an Irish study, Clinical Nursing Research, 2006, pp. 6-26, vol. 15(1).

Boscart et al, Acceptability of a wearable hand wash device with monitoring capabilities, J Hosp Infect, 2008, pp. 216-222, vol. 70.

Boscart et al, Automated hand hygiene monitoring: perspectives for healthcare staff, management, and infection control specialists, J Europ Assoc Hosp Manage 2009, pp. 15-16.

Levchenko et al, Embedded system for hygiene compliance monitoring, IEEE Transactions on Automation Science and Engineering, 2009, (in press).

Boscart et al, Defining the configuration of a hand hygiene monitoring system. American journal of Infection Control, 2009, (in press).

Boscart et al, Advanced technologies to curb healthcare-associated infections. Invited commentary Healthcare Papers, 2009, pp. 51-55, vol. 9(3).

Fernie et al, Technology to reduce institutional cross-infection rates . . . , 6th Conference of the International Society for Gerontechnology, May 20-23, 2008 Pisa, Italy.

Levchenko et al, Distributed IR based technology to monitor hand hygiene of healthcare staff, IEEE TIC STH, 2009, p. 252-255.

Boscart and Levchenko, Advanced technology . . . clinical setting. International Conference & Workshops RNAO, 'Nurses: The Solution . . . Transformation', Oct. 2008, Beijing, China.

Boscart et al, Hand hygiene compliance . . . healthcare staffInstitute for Healthcare Improvement's National Forum on Quality Improvement in Health Care, Apr. 2009, Canada.

Boscart et al, Testing of a portable . . . in the clinical setting. Health Professions Education, Global Best Practices in Simulation, May 2009, Toronto Canada.

Hui et al, Distributed community detection in delay tolerant networks, MobiArch, Aug. 27-31, 2007, vol. 7, Kyoto Japan.

Yoneki et al, Visualizing community detection in opportunistic networks, Chants, Sep. 14, 2007, Montreal Quebec.

Aiello et al, The Influence of knowledge, perceptions, and beliefs, on hand hygiene practices in nursing homes, Assoc Profession Infect Cont Epid 2008.

Assanasen et al, Impact of 2 different levels of performance feedback on compliance with infection control process measures in 2 intensive , AJIC, 2008, pp. 407-413, vol. 36(6).

Backman et al, An integrative review of the current evidence on the relationship between hand hygiene interventions . . . , AJIC, Jun. 2008, pp. 333-348, vol. 36(5).

Cantrell et al, Hand hygiene compliance by physicians: marked heterogeneity due to local culture? AJIC, May 2009, pp. 301-305, vol. 37(4).

Cromer et al, Monitoring and feedback of hand hygiene compliance and the impact on faculty . . . , AJIC, Nov. 2008, pp. 672-677, vol. 36(9).

Pittet and Boyce, Hand hygiene and patient care: pursuing the Semmelweis legacy, The Lancet Infectious Diseases, The Lancet, Apr. 2001, p. 9-20, vol. 1 ( supp 1).

Edwards et al, National healthcare safety network (NHSN) report, data summary for 2006 through 2007, issued Nov. 2008, AJIC, pp. 609-626, vol. 36(9).

Gould et al, Measuring handwashing performance in health service audits and research studies, J Hosp Infection, 2007, pp. 109-115, vol. 66.

Larson et al, Hand Hygiene Behavior in a Pediatric Emergency Department and a Pediatric Intensive Care Unit . . . , Am J Crit Care, Jul. 2005, pp. 304-312, vol. 14(4).

Haas and Larson, Measurement of compliance with hand hygiene, Journal of Hospital Infection, 2007, pp. 6-14, vol. 66.

Forman et al, Qualitative research methods: Key features and insights gained from use in infection prevention research, AJIC, Dec. 2008, In press.

Gould et al, Interventions to improve hand hygiene compliance in patient care (review), the Cochrane Collaborations, 2007, Issue 7, John Wiley and Sons LTD.

Zoutman et al, A cross Canada survey of infection prevention and control in long-term care facilities, Am J Infect Control, 2009, pp. 358-363, vol. 37.

Zoutman and Ford, A comparison of infection control program resources, activities, and antibiotic resistant organism . . . , AJIC, Dec. 2008, In press.

Zoutman and Ford, The relationship between hospital infection surveillance and control activities, AJIC, 2005, pp. 1-5, vol. 33(1).

Zoutman et al, The state of infection surveillance and control in Canadian acute care hospitals, AJIC, 2003, pp. 266-273, vol. 31(5).

Venkatesh et al, Use of electronic alerts to enhance hand hygiene compliance and decrease transmission . . . ,AJIC, Apr. 2008, pp. 199-205, vol. 36(3).

Siegel et al, Keeping patients safe: an interventional hand hygiene study at an oncology centre, Clin J Oncology Nurs, Oct. 2007, pp. 643-646, vol. 11(5).

Smith and Rusnak, Infection Prevention and Control in the Long-Term-Care Facility, Infect Control Hospital Epidemiology, 1997, pp. 831-849, vol. 18.

Kohan et al, The importance of evaluating product dispensers when selecting alcohol-based handrubs, AJIC, Oct. 2002, pp. 373-375, vol. 30(6).

Swoboda et al, Isolation status and voice prompts improve hand hygiene, AJIC, Sep. 2007, pp. 470-476, vol. 35(7).

Whitby et al, Behavioural considerations for hand hygiene practices: the basic building blocks, Journal of Hospital Infection, 2007, pp. 1-8, vol. 65.

Whitby et al, Three successful interventions in healthcare workers that improve compliance with hand hygiene: Is sustained replication possible?, AJIC, 2008, pp. 349-355, vol. 36.

World Health Organization, Who Guidelines on Hand Hygiene in Health Care (Advanced Draft): A Summary, Who, 2005, France.

Medonyx, http://www.medonyx.com/newsite/index.htm, 2006, Toronto.

Trick et al, Multicenter Intervention Program to Increase Adherence to Hand Hygiene . . . , Infection Control and Hospital Epidemiology, Jan. 2007, pp. 42-49, vol. 28(1).

Plaggemeier, MRSA: a big bad bug, Long Term Care, Jun./Jul. 2008, pp. 21-23, vol. 18(2).

McGuckin, The effect of random voice hand hygiene messages . . . , AJIC, Dec. 2006, pp. 673-675, vol. 34 (10).

Lent et al, Evaluation of patient participation in a patient empowerment initiative to improve hand hygiene practices . . . , AJIC, Mar. 2008, In press.

Kryski, Infection control: Protection through Prevention, Long Term Care, Jun./Jul. 2008, pp. 19-20, vol. 18(2).

Jang et al, Focus group study of hand hygiene practice among healthcare workers in a teaching hospital in Toronto, Infect Control Hosp Epid, Feb. 2010, pp. 144-150, vol. 31(2).

Chagpar, A Human Factors Approach to Hand Hygiene, PowerPoint presentation for the University Health Network, 2008, Toronto.

Bleak et al, An innovative method of measuring and improving hand hygiene adherence using a personal point of care, 2007, California.

Brock, The impact of performance feedback on Handwashing behaviors, Dissertation, the University of Alabama at Birmingham, 2002.

Cagle, The personal responsibility paradigm shift; Nursing and Patient Care, Jul. 2007, pp. 42-48.

Aiello, Casual inference: the case of hygiene and health, AJIC, Dec. 2002, pp. 503-510, vol. 30(8).

MMWR, Guideline for Hand Hygiene in Health-Care Settings: . . . ,Centers for Disease Control, Oct. 25, 2002, vol. 51( No. RR-16), Atlanta, Georgia.

Rebelo, Shea 2009: New Device Monitors Hand-Hygiene Compliance by Healthcare Workers, http://www.medscape..com/viewarticle/589931, Presented Mar. 20, 2009.

CTV News, Device reminds health workers to wash hands, http://www.ctv.ca/servlet/ArticleNews/story/CTVNews/20080303/hand, 2008, Toronto.

Hui and Crowcroft, Bubble Rap: Forwarding in small world DTNs in ever decreasing circles, Technical Report from the University of Cambridge, May 2007, No. 684.

Pittet, Improving Adherence to Hand Hygiene Practice: A Multidisciplinary Approach, Emerging Infectious Diseases, Mar./Apr. 2001, p. 234-240, vol. 7(2).

Haas and Larson, Impact of Wearable Alcohol Gel Dispensers on Hand Hygiene in an Emergency Department, Academic Emergency Medicine, Apr. 2008, pp. 393-396, vol. 15 (4).

Kuttenkuler, Hand Hygiene Monitor Tested at VCU Medical, http://www.news.vcu.edu/news/Hand_Hygiene_Monitor_Tested_at_VCU_Medical_Center, Sep. 16, 2009, VCU Communications.

Priest, After the beep, please record your hand hygiene, http://www.theglobeandmail.com/servlet/story/RTGAM.20080303., Mar. 3, 2008, Toronto, Phillip Crawley, Publisher.

CBC News, Electronic handwashing tool could curb superbug spread, http://www.cbc,ca/health/story/2008/03/03/handwashing-system.html, Mar. 3, 2008, Toronto.

Hotchkiss et al, Pathogen Transmission and Clinic Scheduling, Emerging Infectious Diseases, Jan. 2006, pp. 159-162, vol. 12(1).

Huskins, Interventions to prevent transmission of antimicrobial-resistant bacteria in the intensive care unit, Curr Opin Crit Care, 2007, pp. 572-577, vol. 13.

Larson et al, An organizational climate intervention associated with increased handwashing . . . , Behavioral Medicine, Spring 2000, pp. 14-22, vol. 26(1).

Larson, A tool to assess barriers to adherence to hand hygiene guideline, Am J Infect Control, Feb. 2004, pp. 48-51, vol. 32(1).

Murphy et al, Building the infection prevention system of tomorrow: Proceedings of the 2007 APIC Futures Summit, AJIC, May 2008, pp. 232-240, vol. 36(4).

Mayhall, C.G., Hospital Epidemiology and Infection Control, 3rd Edition, Chapter 96, by Manfred L. Rotter "Hand washing and hand disinfection", pp. 1727 to 1746 (2004).

Snyder, Hardwiring hand hygiene among staff members, Nursing Management, Feb. 2008, p. 14, vol. 39(2), Publisher:(C) 2008 by Lippincott Williams & Wilkins, Inc.

Joint Commission, Measuring Hand Hygiene Adherence: Overcoming the Challenges, 2009, Consensus Measurement in Hand Hygiene (CMHH) project, Oakbrook Terrace, Illinois.

Inuzuka, Research on healthcare worker behavior to increase hand hygiene . . . ,Poster presentation/publication 9-122, Education and Int'l Conference, Jun. 24, 2008.

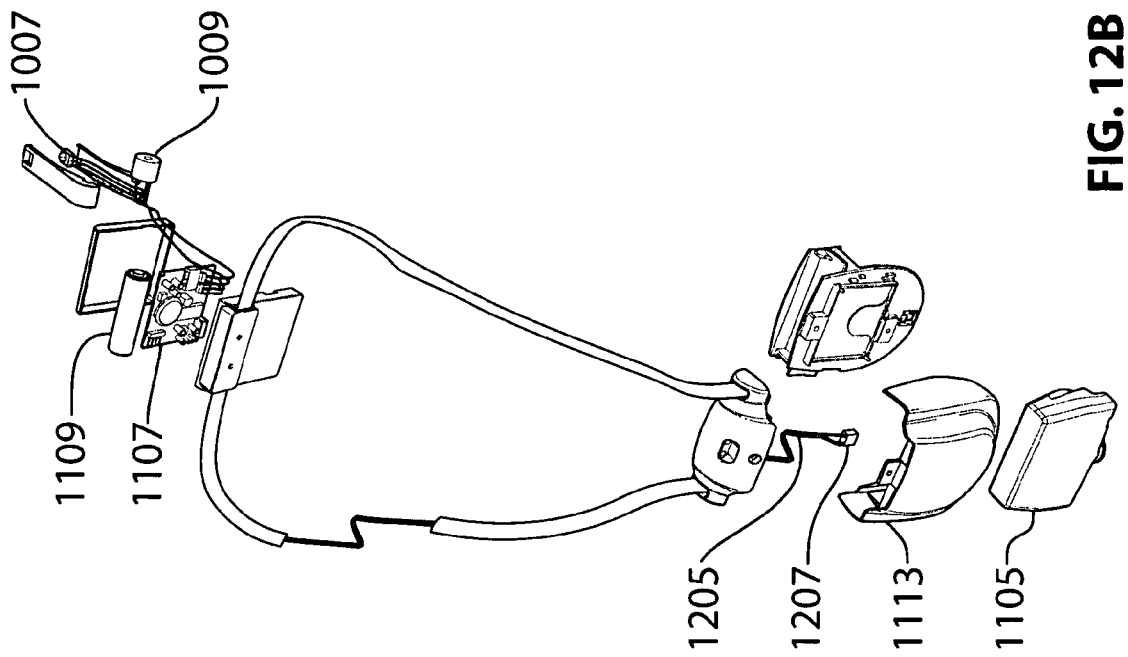
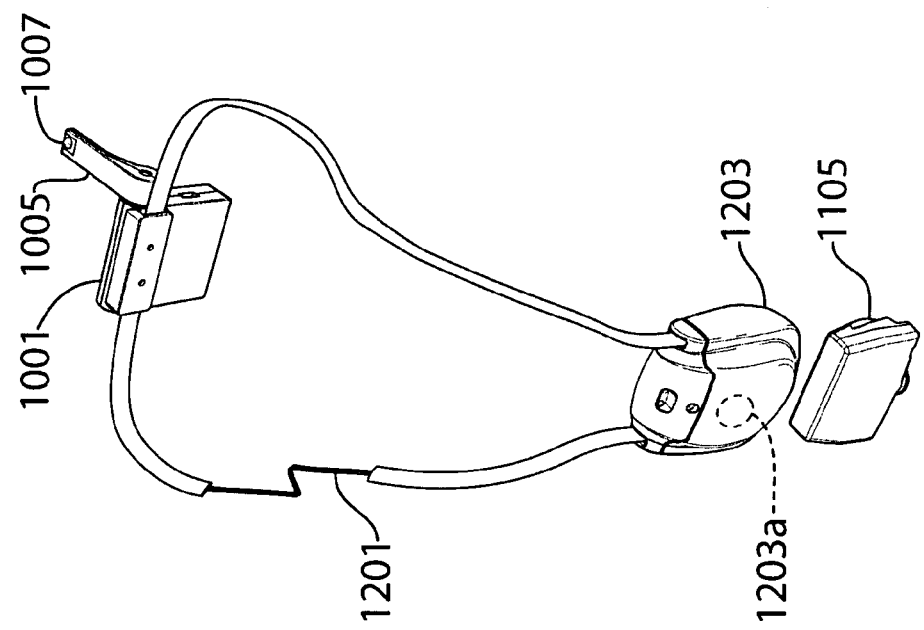
FIG. 12A
FIG. 12B

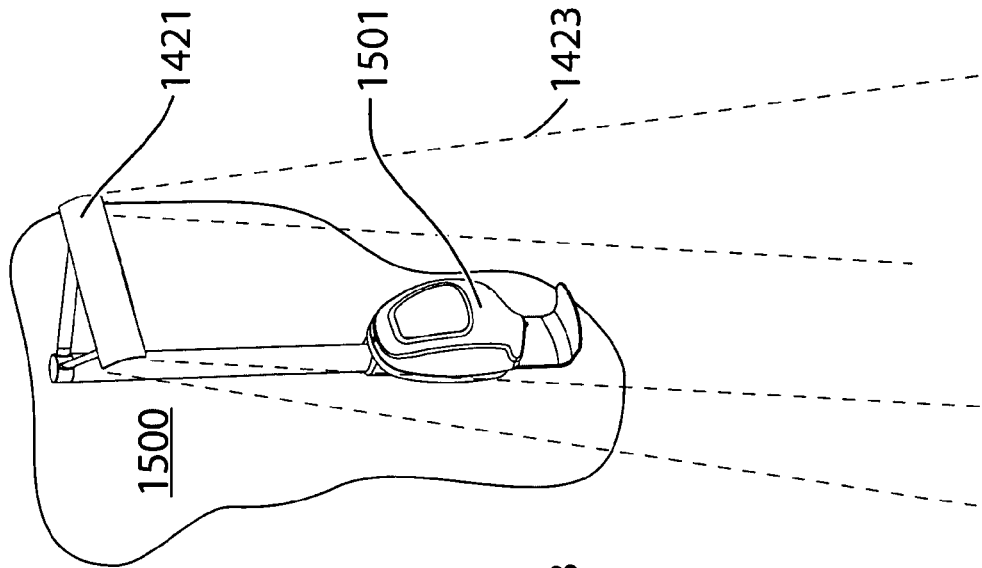
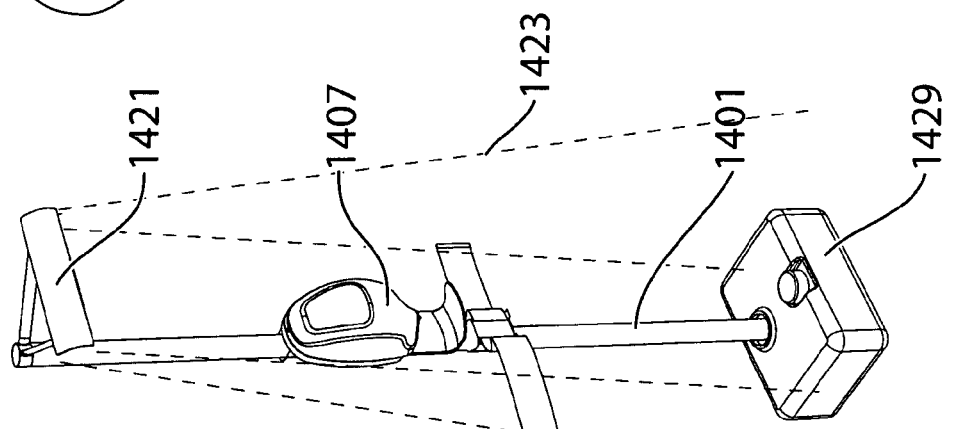
FIG. 15A
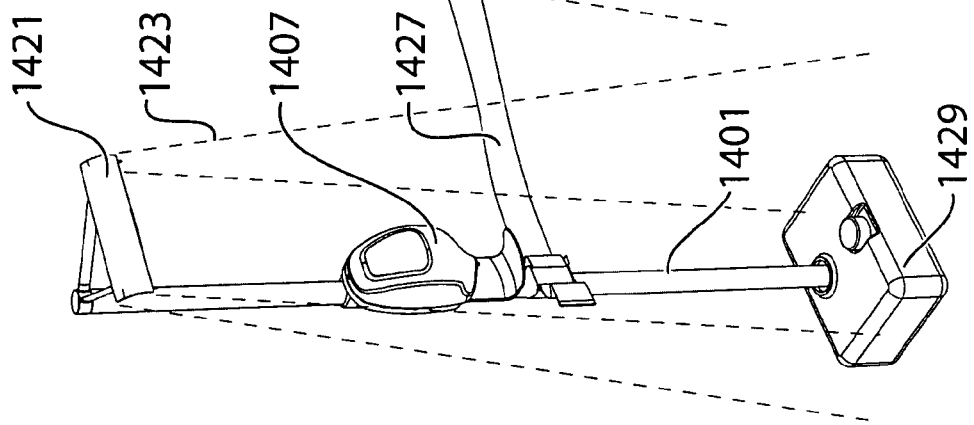
FIG. 15B

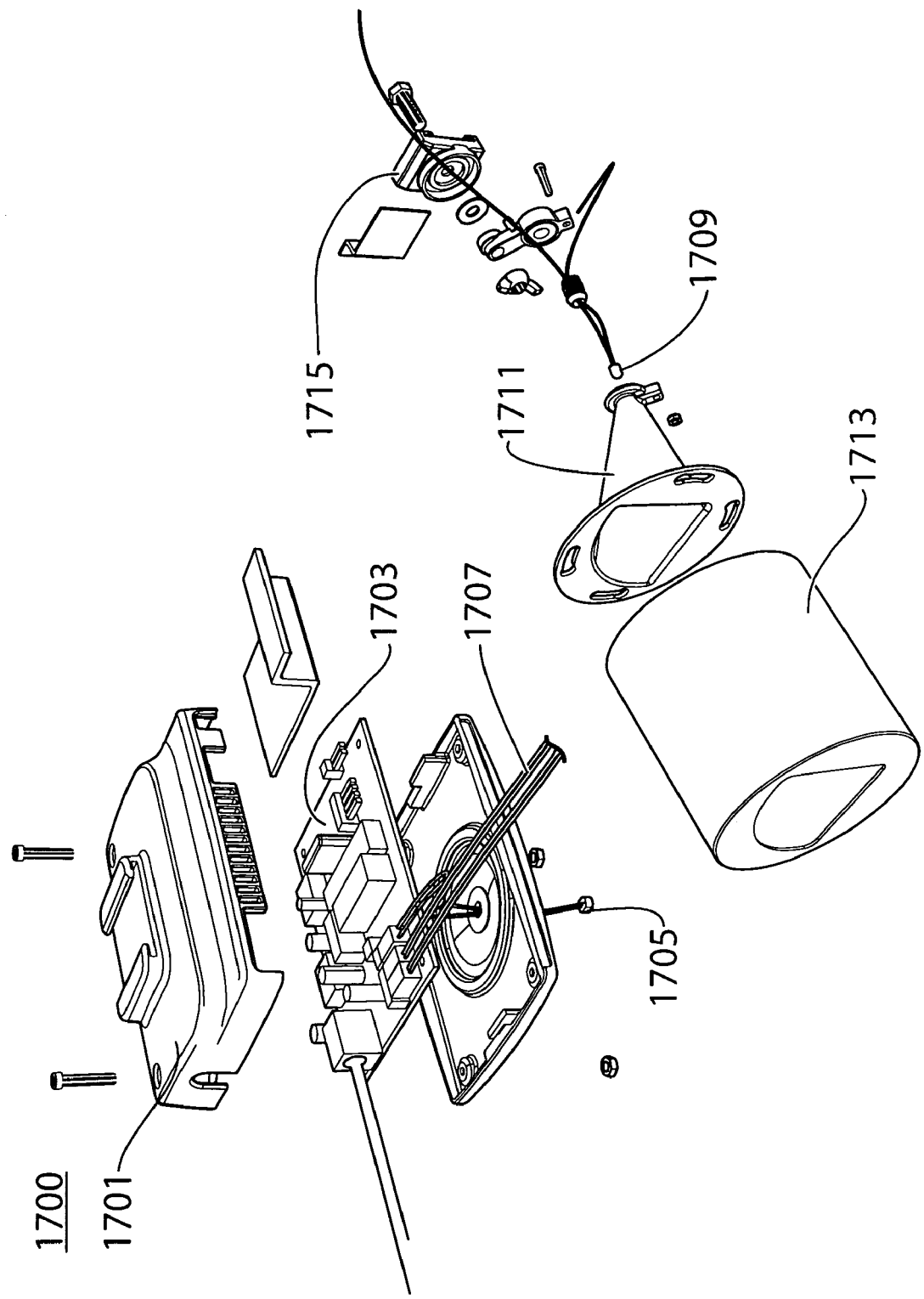

HAND HYGIENE COMPLIANCE SYSTEM

REFERENCE TO COPENDING APPLICATIONS

The entire subject matter of U.S. Provisional application 60/920,779 filed Mar. 30, 2007 and entitled HAND HYGIENE COMPLIANCE SYSTEM is incorporated herein by reference. The entire subject matter of U.S. Provisional application 60/960,521 filed Oct. 2, 2007 and entitled HAND HYGIENE COMPLIANCE SYSTEM is also incorporated herein by reference. The applicants claim priority benefit under Title 35, United States Code, Section 119 of the above applications.

TECHNICAL FIELD

The present invention relates to hand hygiene systems and more specifically to hand hygiene monitoring systems.

BACKGROUND OF THE INVENTION

Approximately one in 10 people admitted to hospitals in the United States acquire a new infection during their stay. These nosocomial infections result in an estimated 100,000 deaths per year in the United States. Nosocomial infections increase the length of patient stays in hospital, contributing to increased healthcare staffing levels, increased costs and increased use of resources. This situation contributes significantly to the overall stress on the healthcare systems and increases wait times. It is estimated that approximately half of these nosocomial infections are the result of inadequate hand hygiene compliance by healthcare staff.

There is considerable evidence that hand hygiene compliance is a primary means to reduce nosocomial infections and the transmission of pathogens. Pathogens are normally present on the skin of healthcare workers and patients and on surfaces surrounding the patient. These organisms can be transferred to healthcare workers' hands where they can survive for periods ranging from minutes to hours. The final step in the transmission process is the transfer of organisms from the contaminated hands of the caregiver to other patients or clean environmental surfaces. Alcohol-based hand rubs seem to be significantly more effective than washing with soap and water and in the reduction of transmission of pathogens.

Wearable dispensers of alcohol-based hand rub can provide ready access hand hygiene without the need to visit a fixed hand washing station and can reduce the time required to perform hand hygiene especially for busy staff such as nurses.

Unfortunately, published studies have generally found that compliance with hand hygiene requirements by healthcare workers averages about 40%. Various traditional educational and management interventions can increase awareness and improve this in the short term but generally do not provide sustainable improvements.

Some prior art systems such as U.S. Pat. No. 5,392,546 to Smith, entitled "Hand Washing Compliance Measurement and Monitoring System" monitor compliance but have several possible disadvantages. A possible disadvantage of the system of Smith is that there is either no prompting of the user when it is necessary to perform hand washing, or the user is prompted every time they enter a zone, irrespective of whether they performed appropriate hand washing or not. Neither scenario would seem to encourage the user or caregiver to improve hand washing compliance. Other possible disadvantages of the system of Smith are interference between site ID transmitters between closely spaced sites and lack of a method to prompt users to wash their hands after extended periods of time within the same zone.

Accordingly, an improved system and method to encourage increased hand hygiene compliance in environments where the transfer of pathogens can be dangerous, remains highly desirable.

SUMMARY OF THE INVENTION

It is therefore an object of the present invention to provide an improved system and method to encourage increased hand hygiene compliance by increased convenience and appropriate prompting when needed.

Accordingly, an aspect of the present invention provides a method of encouraging compliance of hand hygiene in a system having a disinfectant dispenser, a dispensing detector, a wearable zone sensor, a controller, a timer means and an alerting means. The method comprises steps of detecting a change of zone of the wearable zone sensor; responsive to detecting a change of zone, starting a preset first timer; and responsive to expiration of the first timer, activating the alerting means.

Another aspect of the present invention provides a method of encouraging compliance of hand hygiene in a system having a disinfectant dispenser, a dispensing detector, a wearable zone sensor, a controller, a timer means and an alerting (prompting) means. The method comprises a system for precisely defining zones around different patients, entrance ways, equipment and other specific areas where hand cleansing is needed. The method also comprises steps of starting a timer when the hand hygiene system is used; prompting for repeated hand cleansing if the timer has expired when entering a zone; detecting the entry of a wearable zone sensor moving into a defined zone; and prompting for hand cleansing when entering a new patient zone or when leaving the room through a zone marking the entrance or leaving the bathroom.

Some embodiments further comprise a step of disabling the first timer responsive to sensing dispensing of disinfectant.

In some embodiments, the step of detecting a change of zone further comprises steps of: sensing a zone identifier signal; decoding a first zone identifier from the zone identifier signal; comparing the first zone identifier with a stored zone identifier; determining a change of zone if said first zone identifier differs from said stored zone identifier; and storing said first zone identifier as the stored zone identifier.

Some embodiments further comprise a step of logging the time associated with detecting a change of zone.

Some embodiments further comprise a step of logging the time associated with activating the alerting means.

Some embodiments further comprise a step of logging said first zone identifier associated with detecting a change of zone.

Some embodiments further comprise a step of transmitting said zone identifier signal from a zone transmitter.

In some embodiments, the step of transmitting comprises transmitting an ultrasonic signal.

In some embodiments, the step of transmitting comprises transmitting a radio frequency signal.

In some embodiments, the step of transmitting comprises transmitting an infrared signal.

In some embodiments, the step of transmitting comprises transmitting an infrared signal from an array of one or more infrared emitters.

In some embodiments, the step of transmitting comprises transmitting said infrared signal within a zone defined by a radiation pattern of each of said infrared emitters.

In some embodiments, the disinfectant dispenser is integrated with said wearable zone detector, the method further comprising sensing dispensing of disinfectant by way of a contact closure.

In some embodiments, the disinfectant dispenser is separate from the wearable zone detector, the method further comprising steps of at said disinfectant dispenser, transmitting an indication of dispensing of disinfectant to said wearable zone detector, and at said wearable zone detector, receiving said indication of dispensing.

In some embodiments, the transmitting of said indication of dispensing of disinfectant is performed wirelessly.

In some embodiments, the wireless transmitting of said indication of dispensing of disinfectant uses radio frequency, infrared or visible spectrum radiation, such as by the use of light emitting diodes (LED's) or the like.

In some embodiments, the receiving of said indication of dispensing, is performed by the infrared sensor of said zone sensor.

In some embodiments, the indication of dispensing is an infrared signal distinguishable from said zone identifier signals.

A further aspect of the present invention provides a system for encouraging compliance of hand hygiene. The system comprises: a disinfectant dispenser; a dispensing detector configured to detect operation of said disinfectant dispenser; a controller in communication with said dispensing detector; a wearable zone sensor in communication with said controller; an alerting device in communication with said controller; and a zone identification transmitter configured to transmit a zone identification capable of detection by said zone sensor when said zone sensor is within a predefined proximity to said zone identification transmitter, wherein said system is configured to activate said alerting means responsive to said dispensing detector not sensing operation of said disinfectant dispenser within a first predefined time delay of said wearable zone sensor detecting a change of zone.

In some embodiments, the system is configured to disable said alerting device responsive to said dispensing detector sensing operation of said disinfectant dispenser.

In some embodiments, the disinfectant dispenser is integral with said wearable zone sensor.

In some embodiments, the disinfectant dispenser is separate from said wearable zone sensor.

In some embodiments, the disinfectant dispenser is mounted in a substantially fixed location and said dispensing detector is configured to transmit indication of operation of said disinfectant dispenser, wirelessly to said controller.

Some embodiments further comprise a data memory in communication with said controller, wherein said controller is configured to log into said data memory, a zone identifier for a current zone associated with said change of zone.

In some embodiments, the controller is configured to log into said data memory, a zone-change time associated with said change of zone, responsive to said change of zone.

In some embodiments, the controller is configured to log into said data memory, a disinfectant dispenser operation time, responsive to sensing operation of said disinfectant dispenser.

Some embodiments further comprise a plurality of zone identification transmitters, each configured to transmit a unique zone identification.

In some embodiments, the zone identification transmitter is configured to communicate with said wearable zone sensor via a wireless signal.

In some embodiments, the wireless signal is an infrared signal.

In some embodiments, each zone identification transmitter comprises an array of one or more infrared emitters.

In some embodiments, each infrared emitter is configured to emit radiation in a predefined zone.

In some embodiments, the predefined zone is determined by a shield having a predefined shape.

In some embodiments, the predefined shape is conical.

In some embodiments, the predefined shape is a fraction of a cone.

In some embodiments, the wireless signal is an ultrasonic signal.

In some embodiments, the wireless signal is a radio frequency signal.

Some embodiments further comprise a communication interface configured to interface with a central computer to permit transfer of said logged information from said data memory to said central computer, and wherein said central computer is configured to process said downloaded data to provide indications of hand hygiene compliance.

Some embodiments further comprise a docking station comprising a plurality of said communication interfaces configured to accommodate a plurality of wearable zone sensors.

In some embodiments, the system is configured to permit anonymous check out and check in of said wearable zone sensors, wherein each said wearable zone sensor comprises a unique identifier.

In some embodiments, the processed downloaded data is retrievable anonymously using said unique zone sensor identifier.

In some embodiments, the processed data for a predefined group of zone sensors is retrievable collectively.

In some embodiments, the system is configured to permit check out and check in of said wearable zone sensors using a user identifier and wherein said system logs said user identifier.

In some embodiments, the system logs said user identifier in said data memory.

In some embodiments, the first predefined time delay is a function of zone type as determined from said zone identification.

In some embodiments, the zone identification comprises a unique number and wherein said zone identification transmitter is configured to transmit said zone identification as a coded sequence of pulses.

In some embodiments, the coded sequence of pulses comprises an integrity check.

In some embodiments, the zone identification transmitter is configured to adapt the output level of said transmitted coded pulses responsive to an ambient radiation level.

In some embodiments, the alerting device is configured to provide an audible signal.

In some embodiments, the alerting device is configured to provide a vibrating signal.

In some embodiments, the alerting device is configured to provide a visual signal, or one or more signals including visual, vibratory, auditory and the like.

In some embodiments, responsive to connection of the communication interface, the controller initiates downloading of the logged information.

In some embodiments, responsive to hand wash dispenser action, the controller resets a first preset timer; resets a second preset timer; resets a third preset timer; and disables alert if active.

In one aspect of the invention, a wearable tag or device is worn by a caregiver or other user in a hospital or other care facility. The wearable tag can detect and log when the caregiver enters or passes through predefined zones and can log when the caregiver sanitizes his hands by detecting activation of a dispensing unit. The dispensing units can be integral to the wearable unit or alternatively can be fixed dispensing units in which case the dispensing unit can transmit indication of the activation of the dispensing unit. In one preferred embodiment, the zones are defined by arrays of infrared (IR) transmitters. The arrays comprise one or more IR emitters with associated collimators/lenses/shields to clearly define a zone. The IR emitters in each zone are controlled by a zone transmitter which modulates the output of the emitters to produce a unique zone identifier.

In some embodiments the step of starting a first timer is responsive to sensing dispensing of disinfectant.

In some embodiments, responsive to connection of a data interface, the controller initiates down load of data to a central computer.

In some embodiments, responsive to disinfectant dispensing action, the controller resets a first preset timer; reset a second present timer; and resets a third preset timer; and disables the alerting device if active.

Another aspect of the present invention provides a wearable smart zone sensor configured to be worn by a user. The smart zone sensor comprises: a zone detector configured to detect a wireless zone identifier signal; a controller in communication with said zone detector; a data memory in communication with said controller; a dispenser activation detector in communication with said controller; and an alerting device in communication with said controller for alerting the user, wherein the controller is configured to: decode a zone identifier from said zone identifier signal; determine when said smart zone sensor enters a zone responsive to said zone identifier signal and store said zone identifier and time of entering in said data memory; determine when said smart zone sensor leaves a zone responsive to said zone identifier signal and store said zone identifier and time of leaving in said data memory; determine when dispenser activation occurs responsive to said dispenser activation detector and store time of dispenser activation in said data memory; and alert said user when a hand cleansing operation is required.

Some embodiments further comprise an interface for transmitting to an external computer, the data stored in said data memory.

Some embodiments further comprise a housing configured as a user identification card.

Some embodiments further comprise a dispenser for hand cleansing product wherein said dispenser activation detector is configured to detect dispensing of said hand cleaning product.

In some embodiments, the dispenser is collocated in said housing with said smart zone sensor.

Some embodiments further comprise a housing for enclosing said smart zone sensor, wherein said housing is configured for attachment to a lanyard.

Some embodiments further comprise an arm pivotally connected to said housing, wherein said arm houses said zone detector and is configured to maintain said zone detector in spaced relationship from said user when said arm is in an operating position and wherein said arm can be pivoted to a storage position.

In some embodiments the zone detector comprises an infrared (IR) sensor.

In some embodiments the dispenser activation detector is configured to receive a wireless signal from a fixed dispenser unit.

In some embodiments the dispenser activation detector is configured to receive an IR signal from said fixed dispenser unit.

In some embodiments the dispenser activation detector is configured to receive a wireless signal from a portable dispenser unit.

In some embodiments the dispenser activation detector is configured to receive a radio frequency (RF) signal from said portable dispenser unit.

In some embodiments the dispenser activation detector is configured for wired communication with a portable dispenser unit, said portable dispenser unit configured for mounting on said lanyard.

Yet another aspect of the present invention provides a fixed dispenser unit for dispensing a hand cleansing product. The fixed dispenser unit comprises: a cleansing product container; a cleansing product dispenser for dispensing said cleansing product from said container; a wireless zone identifier signal transmitter for transmitting a signal indicative of a dispenser activation and zone identifier for receipt by a smart zone sensor; a controller for encoding said zone identifier signal.

In some embodiments, the fixed dispenser unit is configured for mounting on a wall.

In some embodiments, the fixed dispenser unit is configured for mounting on a pylon.

Some embodiments further comprise a proximity sensor for sensing proximity of a user's hands to said dispenser and wherein said controller is further configured to activate said cleansing product dispenser responsive to said proximity sensor sensing a user's hands.

In some embodiments, the fixed dispenser unit is configured for dispensing a viscous product.

In some embodiments, the cleansing product dispenser comprises a pump.

In some embodiments, the wireless zone identifier signal transmitter comprises an infrared emitter.

BRIEF DESCRIPTION OF THE DRAWINGS

Further features and advantages of the present invention will become apparent from the following detailed description, taken in combination with the appended drawings, in which:

FIGS. 12A and 12B illustrate a perspective view and a break-away perspective view respectively, of a lanyard—wearable dispenser embodiment of the present invention;

FIG. 15A illustrates a perspective view of a pylon-mounted fixed dispenser of the present invention;

FIG. 15B illustrates a perspective view of a wall-mounted fixed dispenser of the present invention;

FIG. 17 illustrates a break-away perspective view of an embodiment of a zone controller of the present invention;

It will be noted that, throughout the appended drawings, like features are identified by like reference numerals.

DETAILED DESCRIPTION OF THE PREFERRED EMBODIMENT

Figures 1A, 1B:
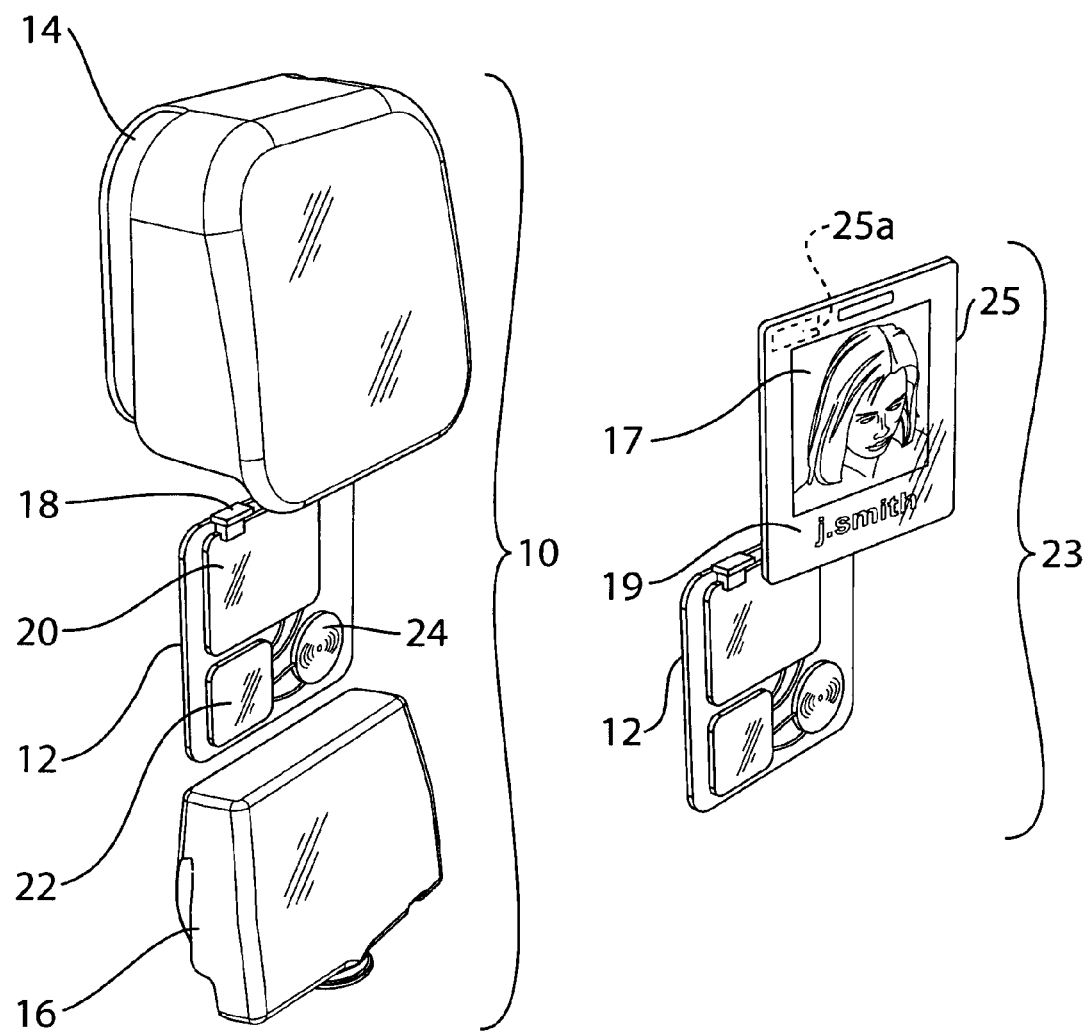
FIG. 1A is a breakaway perspective illustration showing an embodiment of a smart zone sensor incorporating a wearable handwash dispenser of the present invention.
FIG. 1B is a breakaway perspective illustration showing another embodiment of a wearable smart zone sensor of the present invention.

It should be understood that the invention is not limited in its application to the details of construction and the arrangement of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Furthermore, and as described in subsequent paragraphs, the specific mechanical configurations illustrated in the drawings are intended to exemplify embodiments of the invention. However, other alternative mechanical configurations are possible which are considered to be within the teachings of the instant disclosure. Furthermore, unless otherwise indicated, the term "or" is to be considered inclusive.

Various embodiments of the present invention will now be described with reference to the figures. FIG. 1A shows a breakaway perspective illustration of a wearable smart disinfectant dispenser assembly 10. The assembly comprises a smart zone sensor 12 which fits in external housing 14, along with dispenser cartridge 16. The dispenser cartridge 16 is a disposable cartridge for dispensing a hand sanitizing lotion or gel such as alcohol based sanitizing gels well known in the art. The gel is dispensed by squeezing a resilient side wall of the cartridge 16 against external housing 14. The cartridge 16 can be easily replaced as needed. In other embodiments, the cartridge 16 is refillable and reusable. The zone sensor 12 has a signal detector 18, a control circuit 20, a dispensing sensor 22, and an alerting device 24. The detector 18 will be discussed in its exemplified form as an infrared detector 18, though it may also be operable to receive signals of other forms, such as ultrasonic signals. The infrared detector 18 can be a intelligent infrared detector integrated circuit as is well known in the art. The control circuit uses a microprocessor with a real-time clock or other suitable controller. The control circuit 20 is connected to infrared detector 18 which is visible external to the external housing 14 so that the infrared detector 18 can receive infrared signals from among a plurality of zone transmitters 26 (see FIGS. 2, 7, 8) which can be set up in a hospital, or other caregiver environments or food handling environment where hand hygiene might be important to counteract cross contamination. The control circuit 20 is connected to dispensing sensor 22, which is shown here as a pressure sensitive switch which is positioned so as to be able to sense the dispensing action of the cartridge when it is operated by the user. The alerting device 24 can be an audible buzzer or sound generating device or a visual indicator such as a lamp or light emitting diode (LED) or a vibrator to provide an alerting signal to the user without unduly distracting patients or attracting attention, or a combination thereof. The control circuit 20 has a data memory 21 (see FIG. 2) for collecting or logging data.

The assembly 10 is operable in a communication network which, in this example, is computer implemented and may be provided in a number of forms, by way of one or more software programs configured to run on one or more general purpose computers, such as a personal computer, or on a single custom built computer, such as programmed logic controller (PLC) which is dedicated to the function of the system alone. A system controlling such a communication network may, alternatively, be executed on a more substantial computer mainframe. The general purpose computer may work within a network involving several general purpose computers, for example those sold under the trade names APPLE or IBM, or clones thereof, which are programmed with operating systems known by the trade names WINDOWS, LINUX or other well known or lesser known equivalents of these. The system may involve pre-programmed software using a number of possible languages or a custom designed version of a programming software. The computer network may be include a wired local area network, or a wide area network such as the Internet, or a combination of the two, with or without added security, authentication protocols, or under "peer-to-peer" or "client-server" or other networking architectures. The network may also be a wireless network or a combination of wired and wireless networks. The wireless network may operate under frequencies such as those dubbed 'radio frequency' or "RF" using protocols such as the 802.11, TCP/IP, BLUE TOOTH and the like, or other well known Internet, wireless, satellite or cell packet protocols. While the assembly 10 collects location data from zone transmitters 26, the assembly may have the ability to determine its location within the facility by use of other locating methods, such as by global positioning system (GPS) protocols or variants or analogs thereof.

Figure 3:
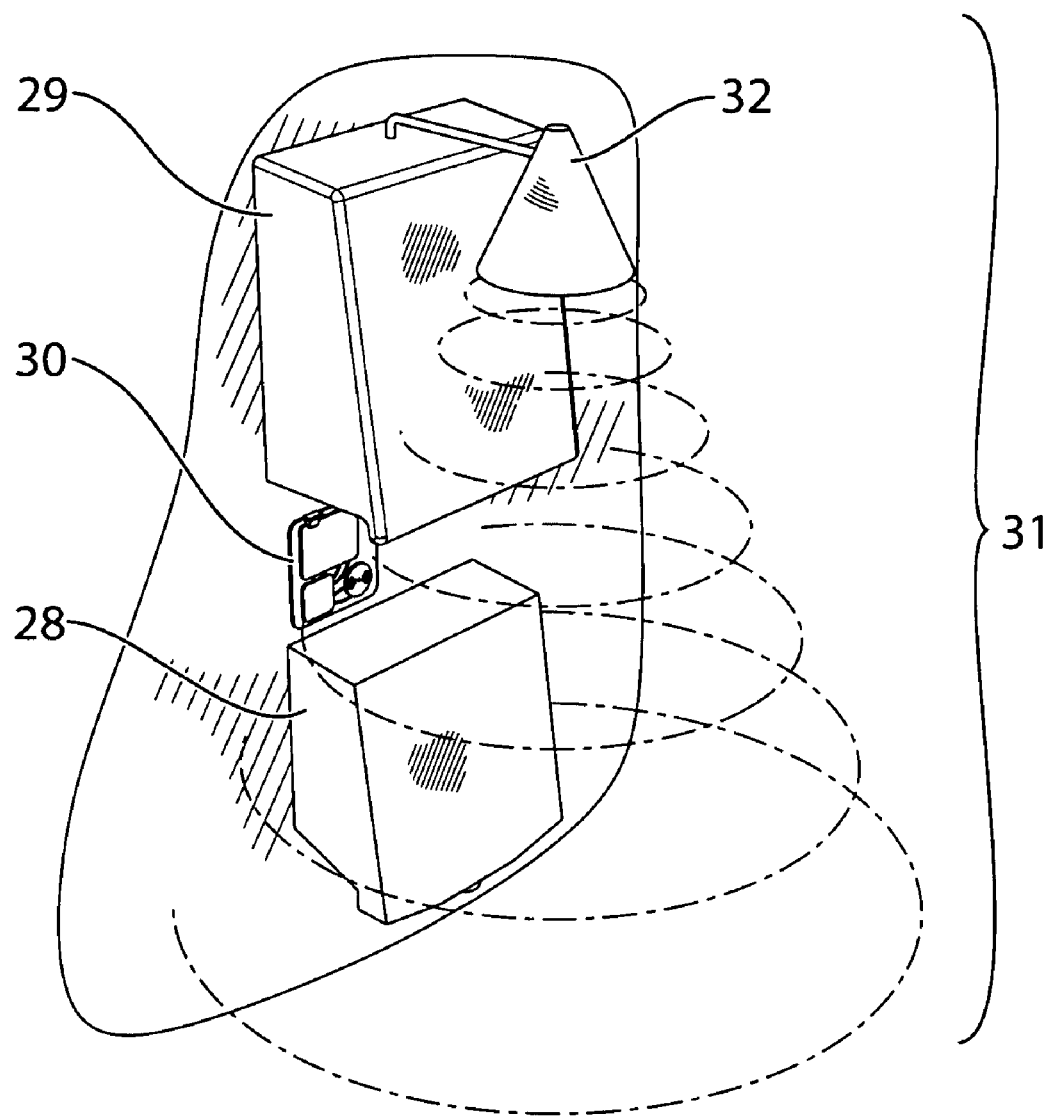
FIG. 3 is a breakaway perspective illustration showing embodiment of a fixed handwash dispenser of the present invention.

In another embodiment, the smart zone sensor 12 can be used independently of the wearable dispenser assembly 10. FIG. 1B illustrates a breakaway perspective view showing a wearable smart zone sensor assembly 23 wherein a wearable housing 25 is configured to accept insertion of smart zone sensor 12 and further configured to accept a clip or lanyard or other suitable attachment means to allow a caregiver or other user to wear the assembly 23. In this embodiment, the wearable smart zone sensor can operate in cooperation with a fixed or wall-mounted disinfectant dispenser 31 as shown in FIG. 3. The wearable smart zone sensor assembly 23 is configured to accept a wireless signal indicating a hand sanitizing operation from an external disinfectant dispenser such as the fixed disinfectant dispenser 31. The wireless signal can be, for example, one or more of a radio frequency signal, an ultrasonic signal, a visible spectrum radiation signal or, as in this particular case, an infrared signal using the infrared detector 18.

The wearable smart zone sensor assembly 23 can be configured as an anonymous device, with a device identifier discreetly incorporated such that a user can readily determine the identity of the unit for later data tracking, but the device identifier not easily visible to other people when it is worn by the user. Alternatively, the wearable housing 25 can be combined with a user identification badge, displaying the user's name 19 and/or photo 17 or other indicia as appropriate to the working environment. The wearable housing 25 can also incorporate magnetic stripes, bar codes or RFID tags, as is well known in the field of user identification badges.

In general, the smart wearable disinfectant dispenser assembly 10, can detect zones that a user enters, such as can be defined around individual patient beds, hospital rooms or patient treatment areas, and can record or log the time of entering and leaving such zones as well as log the zone identifier. Thus, the assembly 10 is operable to detect a change of zone, that is when the user moves from one zone to another. The time of hand sanitizing as determined by activation of the disinfectant dispenser can also be logged.

The alerting device 24 can provide prompting to the user if he/she forgets to sanitize his/her hands when appropriate. If the user sanitizes his/her hands at appropriate times, then the alerting signal is not required and the user can avoid the annoyance of the alerting signal. This feedback can provide a training or conditioning function which can help increase hand hygiene compliance among users. Another feedback mechanism can be reviewing a daily log of hand sanitizing activity correlated with a log of a user's movement between zones. The wearable device of the present invention can be associated with a user identifier or alternatively, can be used anonymously. The user can benefit from the prompting actions of the device and can also review the activity log anonymously by merely accessing logged data associated with an identifier of the device used by the user.

Figure 2A:
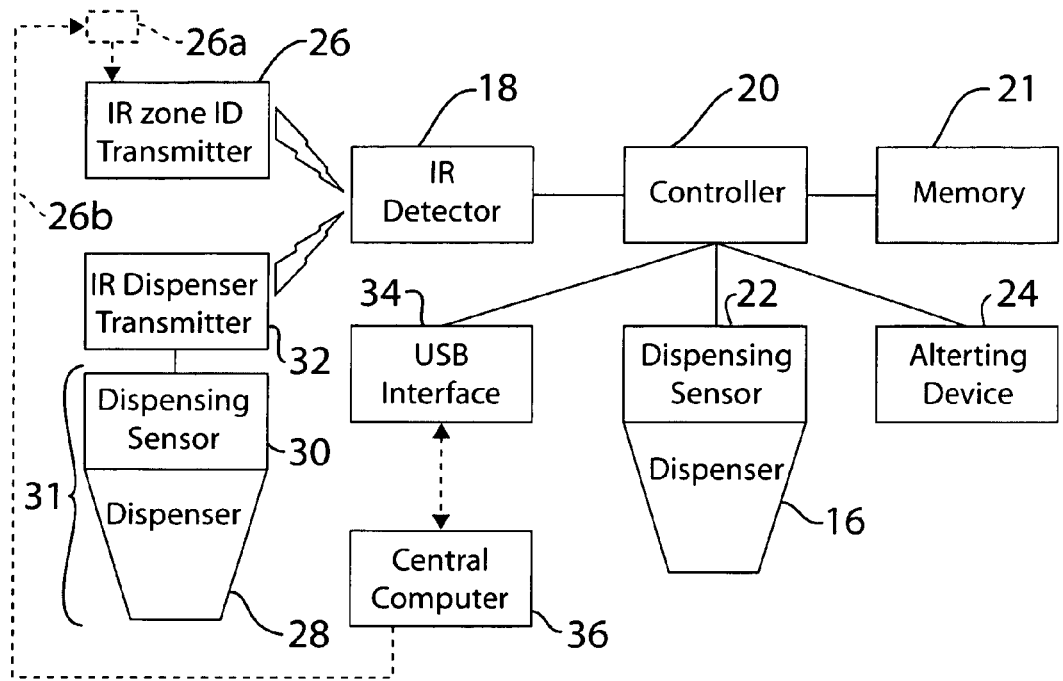
FIG. 2A is a block diagram illustrating a wearable smart handwash dispenser in a system of the present invention.

FIG. 2A is a block diagram illustrating the smart wearable disinfectant dispenser assembly 10 of FIG. 1, in a system of the present invention. Controller 20 has data memory 21 for logging data such as time of dispenser activations, and of entering and leaving zones. The data memory 21 is an EEPROM for non-volatile storage of data although other type of data memory known in the art could be used as an alternative. The data memory 21 can store an identifier code unique to each individual unit, a record or log of the identity of each zone visited and the time of entering and leaving each zone, and a log of the time of dispensing actions or hand hygiene activity history. This data is stored for later downloading to a central computer for later analysis. Temporary data such as hand disinfection status "flags" of the caregiver (clean or dirty) will be stored in the controller 20 so the unit will know whether it has been recently used to disinfect the wearer's hands (this time interval can be set in the software), or whether the wearer's hands have been disinfected since the previous zone was visited. These status flags may be used as a condition for a hygiene status indication light or signal that may be provided on or in association with the wearable device, such as by way of the LED or similar signal indicator shown schematically at 25a in FIG. 1B. Infrared zone identifier transmitters 26 define zones and are configured to emit pulse coded infrared signals to convey zone identifier information to the wearable unit. The coded signals incorporate check sums or other data integrity codes as is known in the art, to provide reliable detection reduce the possibility of false signals. Controller 20 is programmed to demodulate and decode the zone identity signals.

Fixed disinfectant dispenser assembly 31 can be used in conjunction with the smart wearable disinfectant dispenser 10. The fixed disinfectant dispenser assembly 31 can be permanently wall mounted or attached to a patient bed or alternatively, be mounted on a stand or pedestal so as to be available for the user of the smart wearable disinfectant dispenser 10 and to other persons, such as patients or visitors in a hospital. The user of the smart wearable disinfectant dispenser 10 can use the fixed disinfectant dispenser assembly 31 for convenience or if the dispenser cartridge 16 is empty. The user can still benefit from the prompting and data logging features of the smart wearable disinfectant dispenser 10. When the user dispenses disinfecting gel from the fixed dispenser 28 of fixed dispenser assembly 31, this action is sensed by dispensing sensor 30 and a coded signal is sent by infrared dispenser transmitter 32 to the infrared sensor 18 of the wearable device. The coded signal is distinguishable from zone identifier signals. The signal is transmitted for a short period of time, for example, several seconds, to allow the user to ensure the wearable unit captures the signal. Various feedback can be conveyed to the user. The fixed dispenser can have a visual indicator such as an LED to indicate when the infrared dispenser transmitter 32 is transmitting. The controller 20 then decodes the infrared signal and treats this information similarly to receiving an indication from dispensing sensor 22. The user can thus receive credit for disinfecting his/her hands. While the dispenser transmitter 32 is discussed as an infrared transmitter, other transmitters may also be used in some applications, such as ultrasonic or RF transmitters. If desired, the dispensing sensor 22 and controller 20 may be configured to detect when a dispenser is empty.

If desired, the controller may also be operable to decode, in addition to the zone identifier, one or more zone type identifiers in the zone identifier signal. In this case, the alerting device may be operable to issue one or more distinct types of alerts to the user according to the zone type identifier. The one or more zone type identifiers may, for instance, include an identifier that the zone is an isolation region in light of a predetermined communicable disease or condition, such as SEVERE ACUTE RESPIRATORY SYNDROME (SARS) or METHICILLIN-RESISTANT *STAPHYLOCOCCUS AUREUS* (MRSA). For instance, the zone transmitters 26 may be provided with a switch function which controls one or more bits as needed in the zone identifier signal to allow staff to indicate to the system that this particular zone is for an isolated patient, requiring special prompting. The system may then provide a more urgent signal, such as a louder or recognizably different signal when leaving this zone and possibly when approaching a subsequent zone to reduce the probability of transmission by encouraging greater attention to the importance of hand hygiene in this circumstance.

To this end, the plurality of zone identification transmitters may include a first group of one or more zone identification transmitters which are configured to transmit a unique zone type identification. Each of the zone identifiers in the first group may thus include a switch function to adjust the zone type identification. The switch function may include a switch unit located at the zone identification transmitter, as shown schematically at 26a in FIG. 2A, or be remotely adjusted and/or activated by the central computer 36, as shown by the communication path schematically in dashed lines at 26b which may be a wired or wireless communication path.

The controller 20 is provided with communication interface 34. It is shown here as a USB interface but persons skilled in the art will recognize that other interfaces could be used as well. The communication interface 34 can connect to a connector incorporated in a docking station configured to accept one or more smart wearable disinfectant dispenser assemblies 10. The docking station can store the wearable units when not in use, recharge batteries within the wearable units and download the logged data from the data memory 21.

Figure 2B:
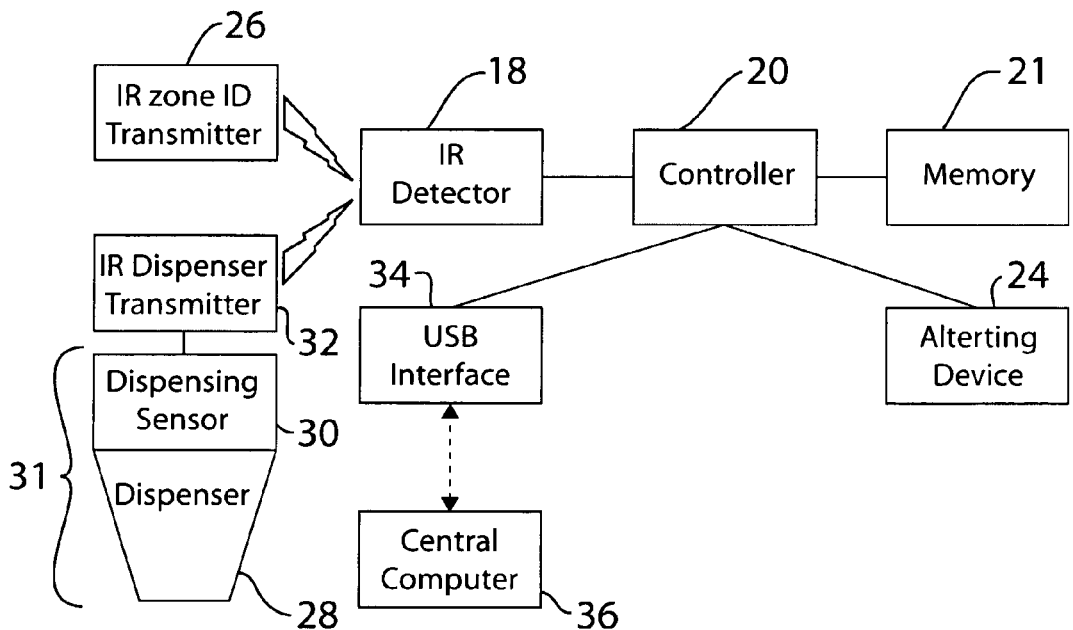
FIG. 2B is a block diagram illustrating a wearable smart zone sensor in a system of the present invention.

FIG. 2B illustrates a similar system to FIG. 2A but the wearable portion has a smart zone sensor without the wearable dispenser portion such as housing 14 and cartridge 16, as shown in FIG. 1B. The dispensing detector or sensor 22 is not required in this scenario and thus can be shielded by housing 25 or alternatively could be disabled by the firmware of controller 20 or alternatively smart zone sensor intended exclusively for use in housing 25 can be manufactured without the sensor 22. The smart zone sensor could be manufactured as a permanent component of housing 25. The wearable smart zone sensor 12 can be incorporated as part of a user's ID badge or could be a plain unit with no easily visible identifier information so that it could be used in an anonymous fashion.

FIG. 3 is a breakaway perspective view of the fixed disinfectant dispenser assembly 31 having a fixed housing 29 suitable for mounting on a wall, pole, pedestal, hospital bed or other suitable location. The fixed housing 29 contains disinfectant dispenser 28, a dispensing sensor assembly 30 and infrared transmitter 32. The dispensing sensor assembly 30 comprises a sensor for sensing a dispensing action of disinfectant dispenser 28, and control circuitry to generate a wireless signal to be transmitted by infrared transmitter 32. The infrared transmitter 32 comprises an infrared emitter and an infrared beam collimator or shield to limit the radiation pattern of the infrared emitter to a region or zone proximate to the disinfectant dispenser assembly 31. In this manner, a user disinfecting his/her hands using the disinfectant dispenser assembly 31 can present his/her wearable smart zone sensor 23 or wearable smart disinfectant dispenser 10 to the zone such that the zone sensor 12 is able to receive the wireless signal indicating that he/she has dispensed disinfectant. Other examples of the device 31 may not require the collimator.

Figure 4:
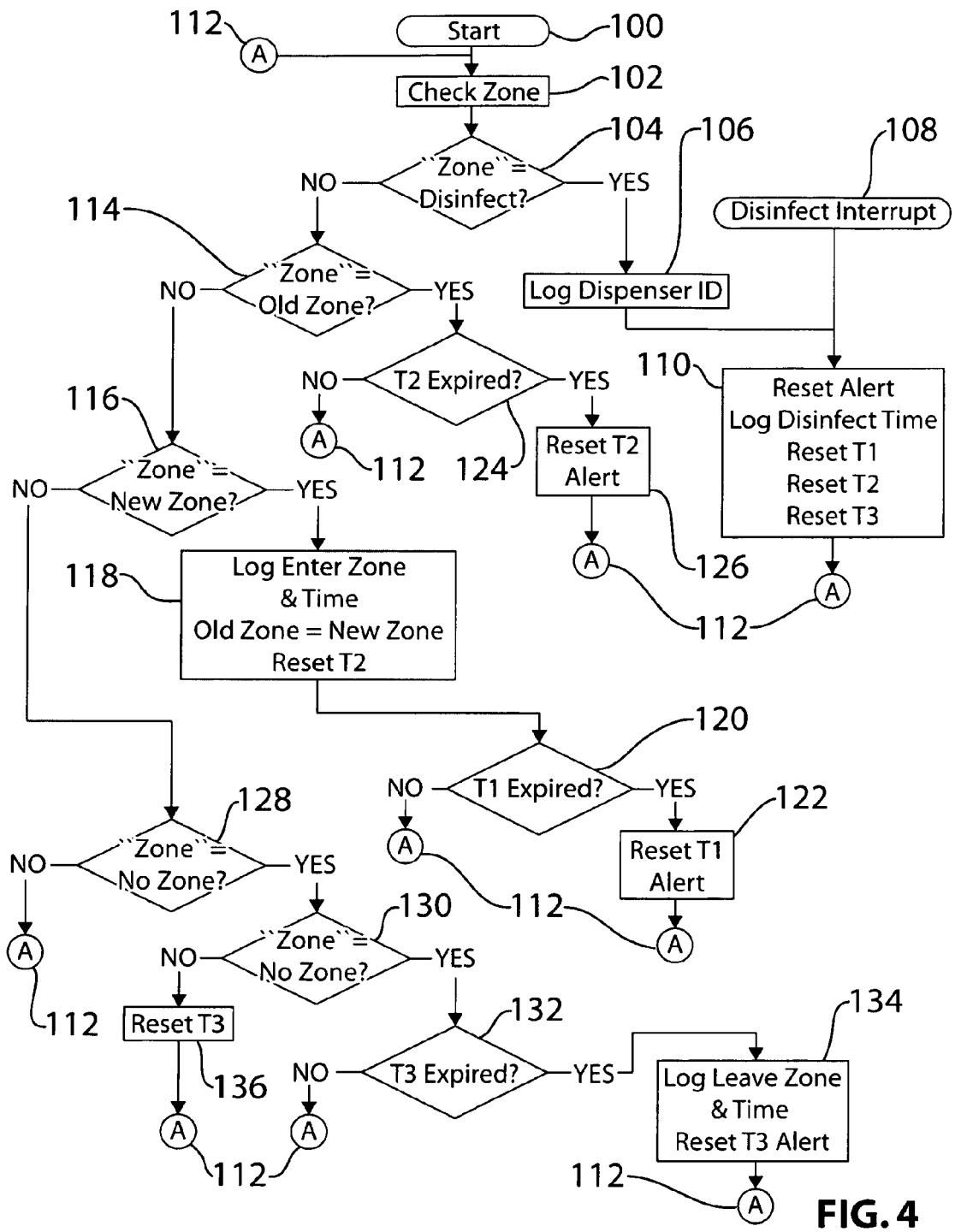
FIG. 4 is flowchart illustrating an embodiment of the present invention.

The operation of an embodiment of the present invention will now be described with reference to FIG. 4. In operation, the wearable smart zone sensor 12 monitors and logs hand disinfecting activity, and entering and leaving zones. The method starts at 100. The controller 20 polls the infrared (IR) detector 18 at step 102. A zone identifier signal is detected infrared detector 18 and demodulated. An example of a suitable zone identifier signal is a pulsed code infrared signal on a 38 kilohertz carrier. A 5 millisecond preamble pulse precedes an 8-bit binary pulse stream representing a zone identifier. This is followed by a second representation of the zone identifier to act as a check-sum and confirm the accuracy of the demodulated zone identifier. One example of a second representation is a pulse stream representing the zone identifier offset by a predefined number. Other check-sum techniques can be used, as is well known in the art, such as inverting the first pulse stream representation. An 8-bit identifier can distinguish up to 256 different zones. More bits can be used for defining zone identifiers as required.

Once a zone identifier has been determined, the controller 20 performs a series of tests starting at 104 where the zone identifier is compared to a "zone identifier" code which is associated with one or more fixed disinfectant dispensers. In one embodiment, one bit of the zone identifier binary representation, represents a disinfectant dispenser, thus if this bit is detected, the decision at step 104 is determined to be "yes" in which case, at step 106, the controller 20 logs the "zone identifier" identifying the dispenser. The process continues to step 110 where the disinfecting action is logged with the associated time of day and date. If the alerting device 24 is activated, it is reset. First timer T1, second timer T2 and third timer T3 are also reset to begin counting down. Note that this functionality can be used with either a wearable smart disinfectant dispenser assembly 10 or a wearable smart zone sensor assembly 23.

First timer T1 represents an acceptable period of time for a user to have disinfected his/her hands in advance of entering a zone, thus a nurse or healthcare worker can sanitize his/her hands while approaching a patient's room. This mechanism can then avoid triggering the alerting device 24 if the healthcare worker is conscientious and efficient. The capability to avoid triggering the alerting device can encourage healthcare workers and other users, to practice good hand hygiene and can possibly help in conditioning such behavior. An example of such a time period is 10 to 40 seconds. This time can be preset and could be configurable by an administrator using an external computer such as computer 36 in FIGS. 2A and 2B.

Second timer T2 represents an acceptable amount of time for a healthcare worker to be inside a zone without sanitizing their hands. Even when restricted to a zone of a single patient, it is possible to cross contaminate the healthcare worker's hands from coming in contact with various bodily fluids, handling open wounds, handling bedpans, etc. The T2 timer can be set to 10 minutes for example.

Third timer T3 represents a time delay before determining that a user has left a zone. A worker could briefly step outside a zone while walking around a patient's bed for example. The wearable zone sensor could be briefly obscured while bending over a patient or by movement of the user. T3 thus "forgives" such intermittent interruptions of a zone signal. The process then returns to the start of the flowchart as indicated by "A" 112.

Step 110 can also be reached by an interrupt signal 108 received from a directly connected dispensing sensor 22 of a wearable smart disinfectant dispenser assembly 10.

If at step 104, the zone identifier is determined not to be a disinfectant dispenser "zone identifier" code, then the process continues to step 114 where the zone identifier is compared to an "old zone" identifier stored in memory 21. If the current zone is the same as the old zone, then the user is still in the same zone and timer T2 is tested at step 124. If T2 has expired then at step 126, timer T2 is reset and the alerting device 24 is activated and the process returns to the start through 112. If the current zone is not the same as the previous zone (old zone) then at step 116, the zone identifier is tested to see if it is a new zone. If yes, at step 118 the current (new) zone is logged in memory 21 along with the corresponding time-of-day and date; the new (current) zone is stored as the old zone; and timer T2 is reset. If the current zone is not a new zone, then at step 128, the zone identifier is tested to determine if not in any zone. If the user is in a recognizable zone, the process continues at the start via 112. If the user is not in a zone, then the process continues at step 130 where the old zone is tested to see if it also was "no zone" in which case timer T3 is tested at step 132 to see if the user has been outside of a zone sufficiently long to make a determination that in fact the user is outside of a zone and not just obscuring the sensor temporarily. If it is determined that the user has left a zone, then at step 134, the time and date of leaving the zone is logged in memory 21; timer T3 is reset; and the alerting device 24 is activated. To avoid activating the alerting device, the user should disinfect his/her hands within the time delay of T3. The process then returns to the start via 112. With timer T2 reset in step 118, the device queries at step 120 if timer T1 has expired. If no, the device advances to step 112. If yes, timer T1 is reset in step 122 and the device proceeds to step 112.

If at step 130, the old zone was not "no zone" then "no zone" is a new condition and the system can not yet determine if the user is actually outside of a zone or is merely obscuring the sensor 18 temporarily in which case at step 136, timer T3 is activated to track the interval during which it is no definitive determination can be made.

Figure 5:
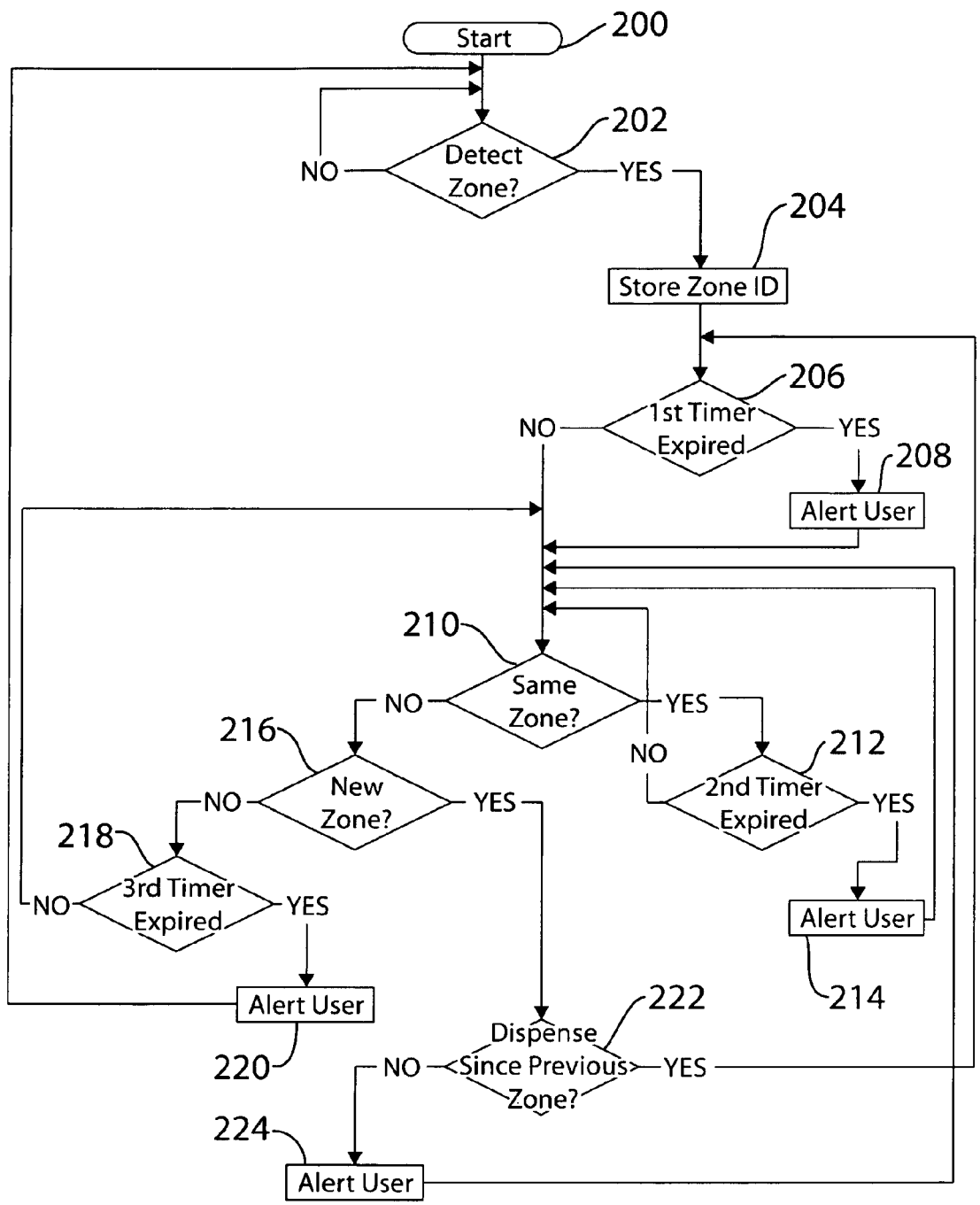
FIG. 5 is flowchart illustrating another embodiment of the present invention.

Another embodiment of the present invention will now be described with reference to FIG. 5. In operation, an embodiment of the wearable smart zone sensor 12 implements the process of FIG. 5, which starts at step 200. At step 202, the controller 20 polls the IR detector 18 to determine if a zone has been detected and if not loops back to step 202 to repeat the step until a zone is detected, in which case the process advances to step 204 where the controller 20 stores the zone identifier (ID) in memory 21. The process continues to step 206 where the controller 20 checks if first timer T1 has expired and if it has, alerting device 24 is activated at step 208. If timer T1 has not yet expired, the process continues to step 210 where the controller 20 tests if the current detected zone is the same zone as the previous zone, that is, the user is still in the same zone. If it is, the second timer T2 is tested at step 212. If timer T2 has not expired, the process returns to step 210. If timer T2 has expired, at step 214, the alerting device is activated and the process returns to step 210. If at step 210, the controller determines that the user is not in the same zone, the process continues to step 216 where the current zone is tested to see if it is a new zone and if not, at step 218 the third timer T3 is tested to see if it has expired. If timer T3 has not expired, the process returns to step 210. If timer T3 has expired the alerting device 24 is activated at step 220 before the process returns to the start of the process at step 202. If at step 216, it is determined that the current zone is a new zone, the system determines at step 222, if the disinfectant dispenser has been activated since the previous zone and if it has, the process returns to step 206. The system can monitor an integral wearable dispenser 16 or a fixed dispenser 28 as previously described. If at step 222, the disinfectant dispenser has not been activated since the previous zone, then at step 224, the user is alerted by alerting device 24, and the process returns to step 210.

Figure 6A:
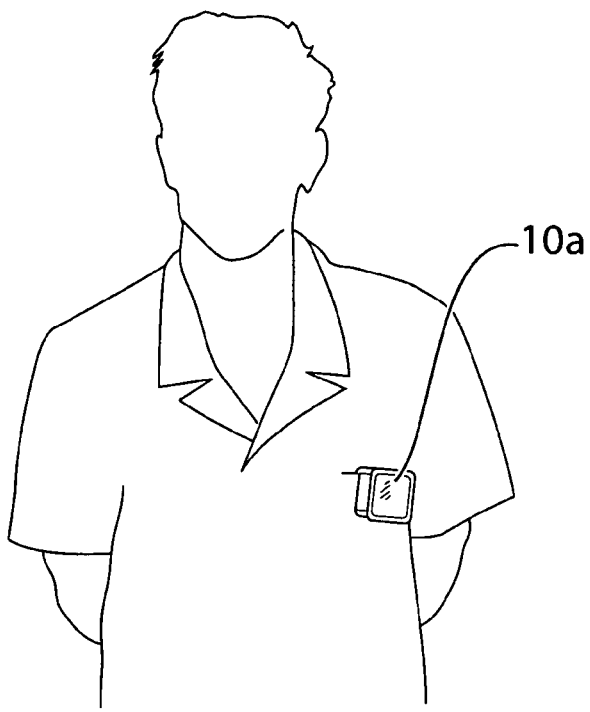
FIGS. 6A, 6B, 6C illustrate various locations for wearing an embodiment of a wearable smart handwash dispenser.
Figure 6B:
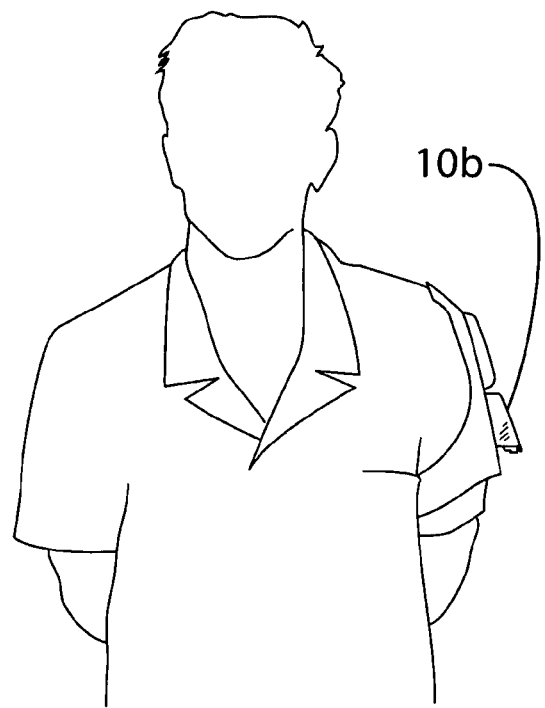
Figure 6C:
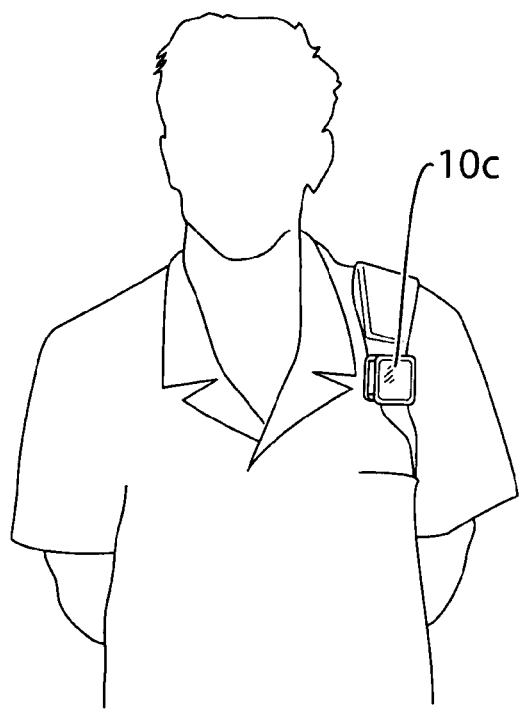

FIGS. 6A, 6B, 6C illustrate how the smart wearable disinfectant dispenser assembly 10 (10a, 10b, 10c) can be worn by a user. The wearable smart zone sensor assembly 23 can be worn in a similar manner. The smart wearable disinfectant dispenser 10a is configured to clip onto a chest pocket on the user's clothing. The smart wearable disinfectant dispenser assembly 10b mounts on the sleeve of the user's clothing by a spring clip, a magnetic pad with a cooperating ferrous metal plate on the inside of the sleeve, with a pin the fabric of the sleeve, via a harness 38 worn over the sleeve or any other suitable means. The smart wearable disinfectant dispenser assembly 10c is mounted on a harness 40 worn on the user's shoulder. In general, it is advantageous to carry the wearable dispenser 10 higher on the user's body so as to be easily accessible for dispensing the disinfecting gel, so as to not interfere with the user's other daily tasks such as to administer care to patients and to best position the infrared sensor 18 to receive infrared signals from overhead zone identifier transmitters.

Figure 7:
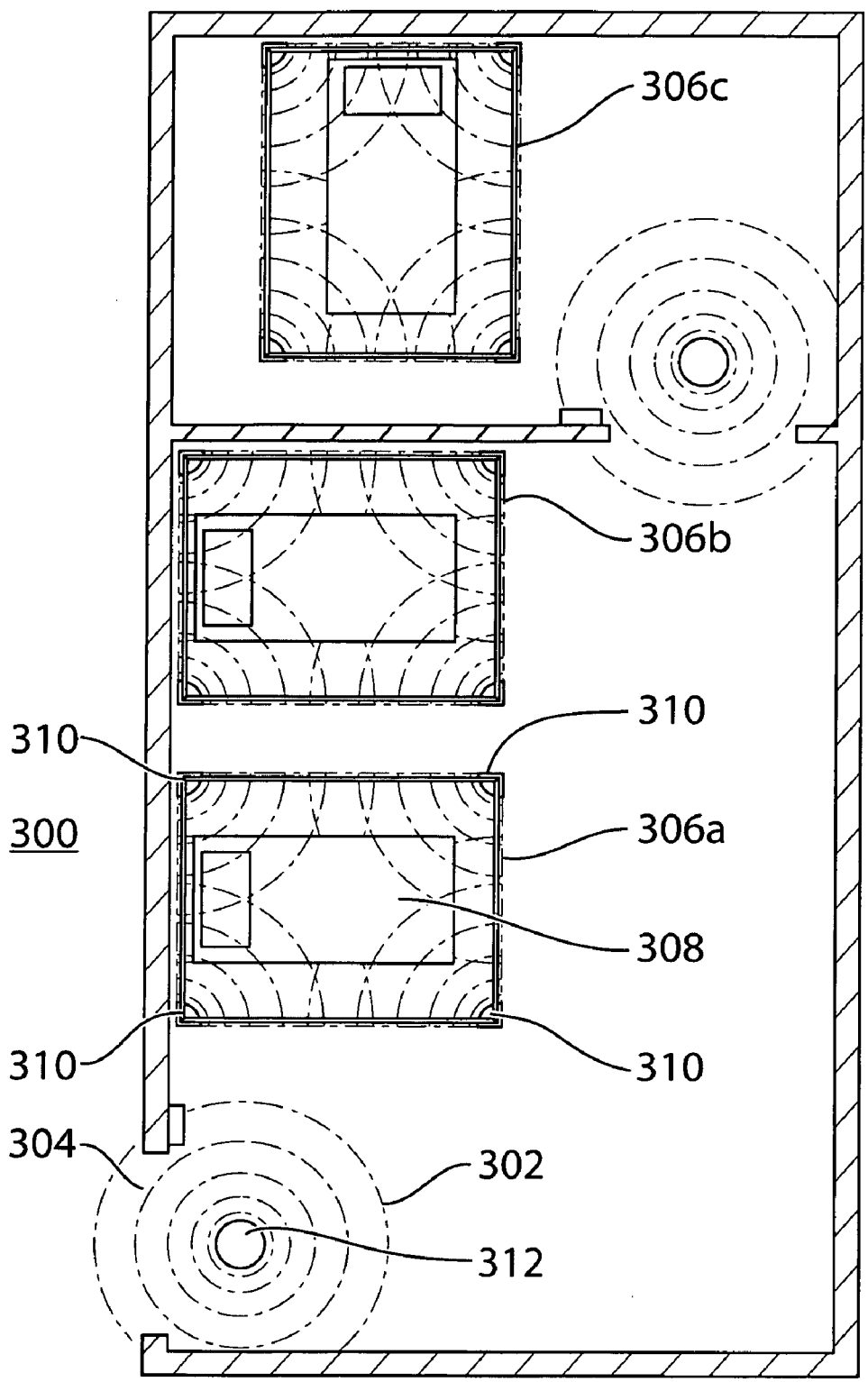
FIG. 7 is a plan view showing an exemplary layout of an embodiment the system of the present invention in a hospital setting.

The layout of zones will now be described with reference to FIG. 7 which illustrates a plan view of an exemplary layout of zones in a hospital setting 300. Zone 302 covers a doorway 304 to a hospital ward or department. Zone 302 is defined by a zone beacon 312 which comprises an infrared emitter driven by a transmitter circuit to modulate the infrared radiation to transmit a signal representing a zone identifier. The emitter of zone beacon 312 can have a shield of conical shape to define a conical zone. Other shapes of shields can be used to define different shaped zones as required. Zone 302 can be coded as a transitional zone and the firmware in the wearable zone sensor can configured to require a disinfecting action only once while moving through the transitional zone 302. A zone 306a can be defined around a patient bed 308 using a zone beacon array of emitters 310, which are described in more detail with reference to FIG. 8. The patient bed zone 306a has clearly defined vertical boundaries which permits adjacent patient bed zone 306b to be located relatively close by without causing interference or overlap of zones. A zone is also shown at 306c around a nearby patient bed.

Figure 8:
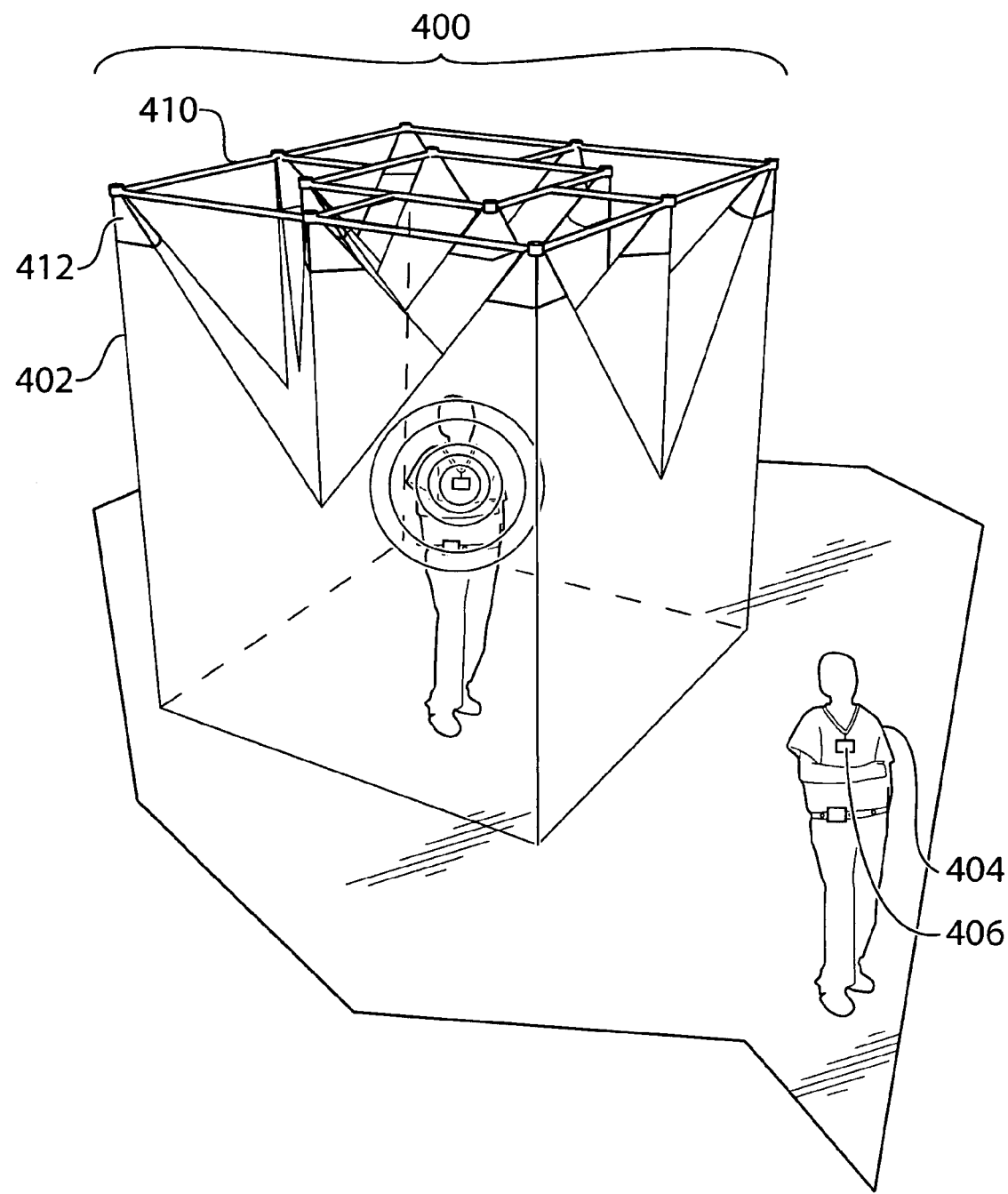
FIG. 8 is a perspective illustration of a zone defined by an embodiment of a zone array of the present invention.

With reference to FIG. 8, a zone 402 is defined by an embodiment of a zone beacon array 400 of the present invention. The zone beacon array (zone array) 400 includes an array of infrared emitters, each having a shield/cone/"collimator" 412 to clearly define the radiation pattern of each infrared emitter. The emitters and associated shields 412 are supported by a frame 410. This arrangement facilitates defining a zone having clearly defined boundaries with vertical walls. It is thus possible to have different zones quite close to one another without overlapping and possibly causing interference. The frame 410 can accommodate wiring to interconnect emitters from the same zone. A common transmitter circuit (not shown) provides the modulated zone identifier signal to drive each of the emitters as discussed previously. The frame 410 can be lightweight and easily suspended from a ceiling and may be integrated into a suspended ceiling as desired. The transmitter can be relatively low powered and be powered from an electrical power outlet with a power supply. A small battery can be supplied to provide uninterruptible power if required.

Figure 9:
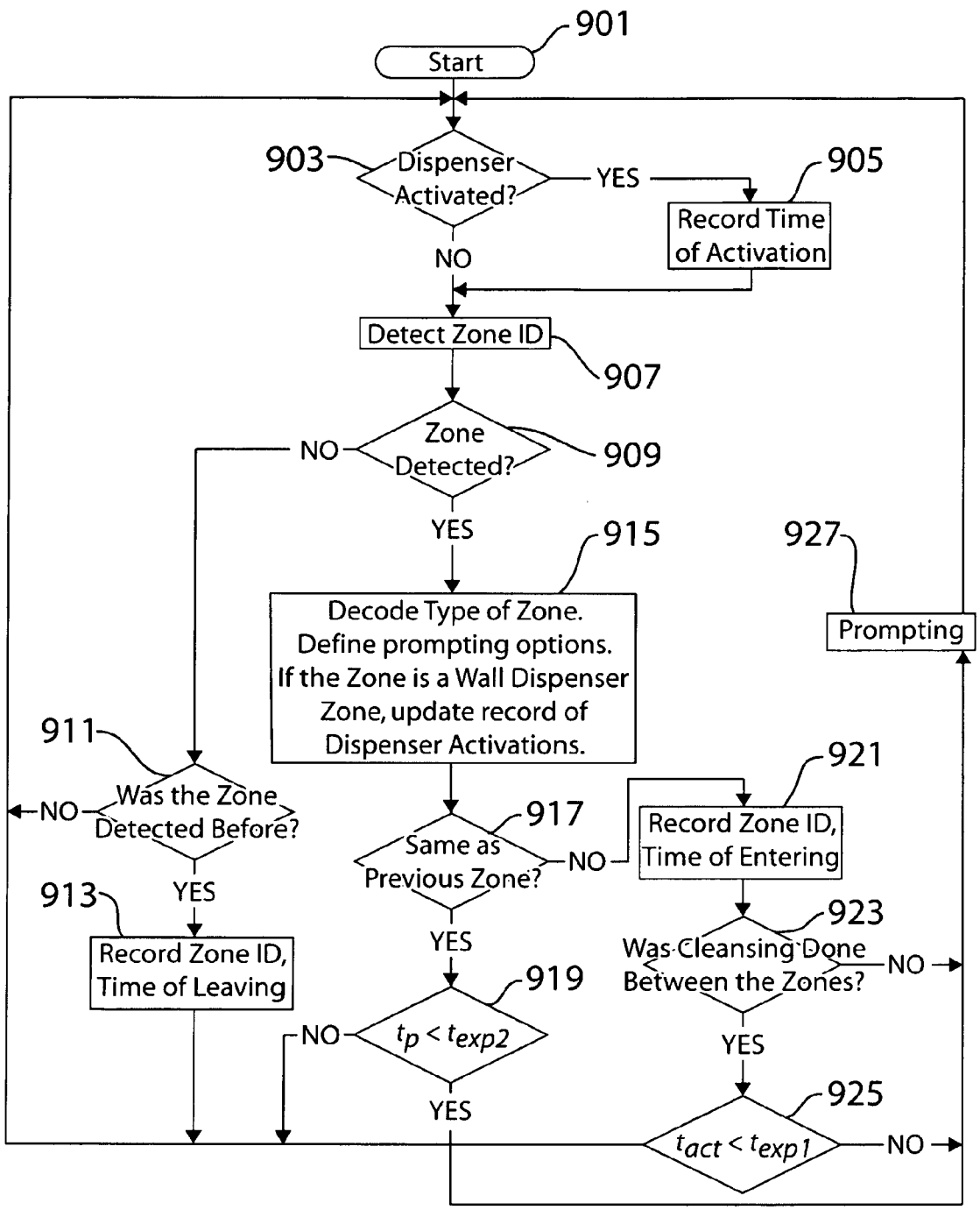
FIG. 9 is flowchart illustrating another embodiment of the present invention.

FIG. 9 is a simplified flowchart illustrating another embodiment of the present invention. The flowchart describes the logic of the wearable smart zone sensor/dispenser operation within the distributed hand hygiene compliance system. In this example, a number of software timers is used to adjust disinfection expiry intervals for different clinical environments, where:

$t_p$ is the time of working with patient (time spent inside the zone);

$t_{exp2}$ is the expiry time inside the zone;

$t_{exp1}$ is the expiry time outside the zone; and $t_{act}$ is the time of dispenser activation.

The device is in sleep mode most of the time and wakes up (or may otherwise be activated) periodically to check the presence of the zone emitters at step 903 with the time of activation recorded at 905. Duration of the power saving intervals is controlled by a watchdog timer and defined by the maximum acceptable reaction time when the user/caregiver enters the zone. The portable unit can also be woken up by an interrupt signal resulting from dispenser activation in the case of a directly connected dispenser. If the zone is detected at step 907 as determined at step 909, the device decodes, at step 915, the type of zone, by being responsive to different signals being emitted from different zones, not only to identify each of them uniquely, but also to classify them as between a full zone, a micro zone or a wall dispenser zone. The device checks, at step 917, to see if the detected zone is the same as the previous zone. The device checks at step 925 that the last disinfection occurred not earlier than the disinfection expiry time texp1 outside of the zone. Note that texp1 is programmable and may vary for different applications. If disinfection was not performed or the time is already expired (step 919) the device prompts the caregiver at step 927 to activate dispenser. When the device leaves the zone its disinfection status flag remains set to clean for a certain programmable period of time, so the caregiver is allowed to leave the zone temporarily and come back without being prompted for disinfection. In this situation if device detects the zone which is different from the previous one at step 917 and dispenser was not activated between the zones (step 923 via step 921 to record the zone ID and time of entering the zone) the disinfection status flag changes immediately issuing the prompting signal (step 927). If the zone is not detected at step 909, then the device queries, at step 911, if the zone was detected before. If yes, then the device records zone ID and the time of leaving at step 913 and reverts back to step 903. If, at step 911, the zone is not detected, then the device reverts back to step 903.

Figure 10:
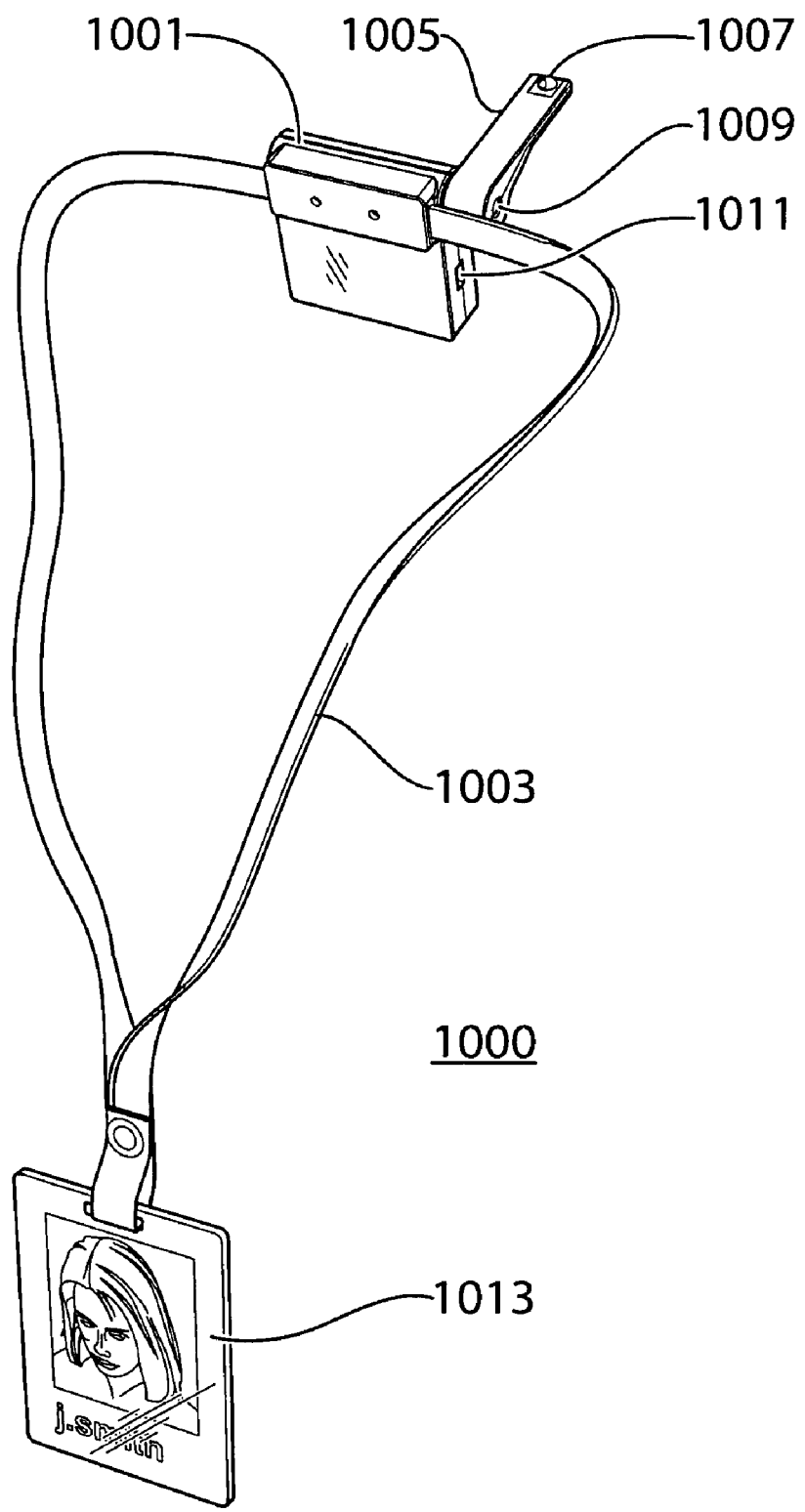
FIG. 10 is a perspective illustration of a lanyard—ID card embodiment of the present invention.

Another embodiment of the present invention is illustrated in FIG. 10 where 1000 is a wearable smart zone sensor. The controller 1107 (not shown) is contained within housing 1001 which is attached to a lanyard 1003, of the type typically used to carry a user identification (ID) card 1013. When this device is worn by a user the controller housing 1001 will be situated behind or near the user's head or lower down the body of the user. Arm 1005 is pivotally attached to housing 1001 and in an operating position it extends outwardly away from the user such that infrared detector or detecting means 1007, or in other words an electronic eye, is clear of the user's head and hair and is in a position to accept infrared signals from zone identifier signal transmitters. In this embodiment an alerting device 1009 such as a beeper is located adjacent to the pivot of arm 1005. A USB connector 1011 is available to connect that device to a reporting means such as an external computer to download stored data. This embodiment can be used by users such as caregivers, patients, visitors in a healthcare facility to prompt the user to sanitize his or her hands when moving from zone to zone. The user can use fixed handwash dispensers of the present intention, mounted on walls near patient zones to sanitize his/her hands. These fixed handwash dispensers can transmit infrared signals indicating that handwashing and was performed, which can be received by the wearable unit and logged.

Figure 11B:
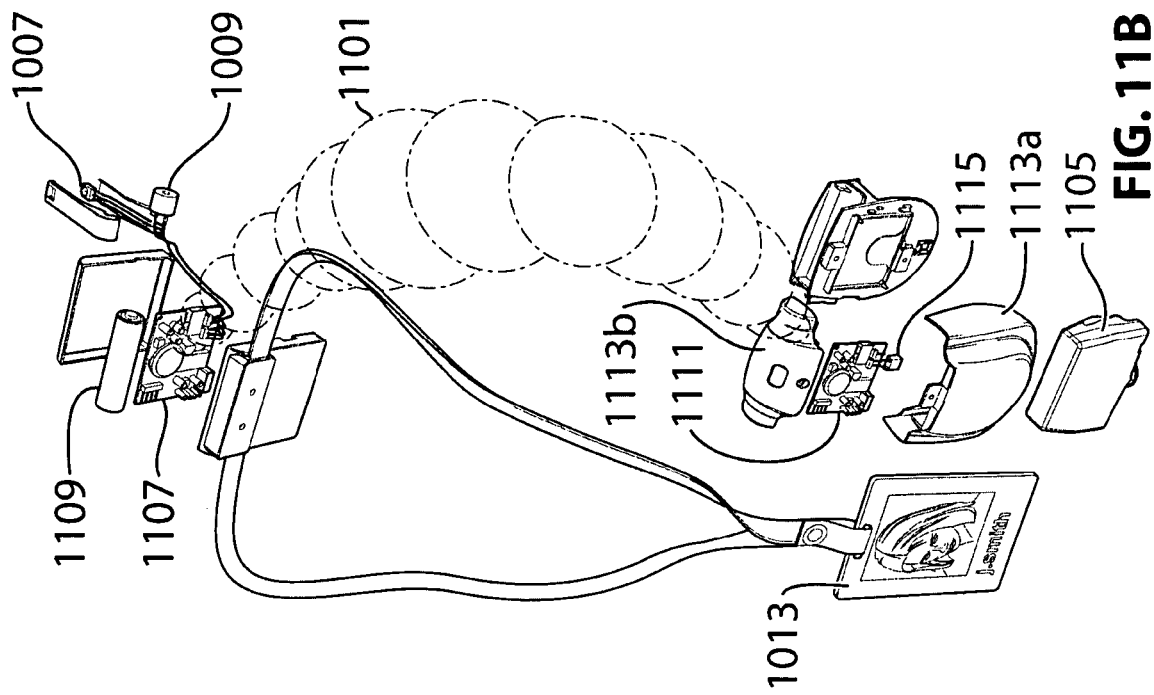
FIGS. 11A and 11B illustrate a perspective view and a break-away perspective view respectively, of a lanyard—ID card with a wearable dispenser with RF communication embodiment of the present invention.
Figure 11A:
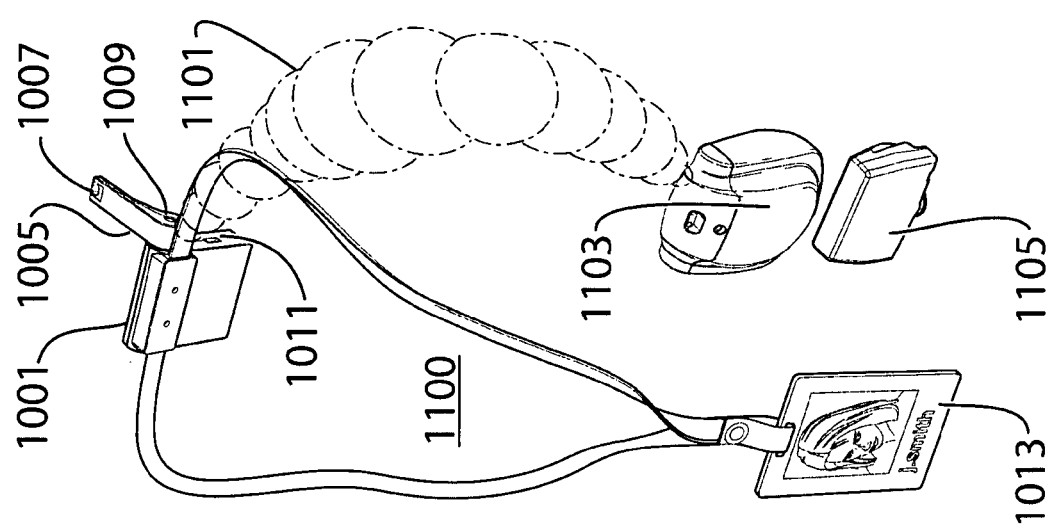

FIGS. 11A and 11B illustrate a perspective view and a break-away perspective view respectively, of another embodiment of a wearable smart zone sensor within housing 1001 and working in cooperation with a corresponding wearable dispenser unit 1103 including dispenser cartridge 1105 and having an RF or other communication link 1101 with the wearable smart zone sensor 1000. This embodiment works similarly to the embodiment of FIG. 10 with the added functionality of having the wearable hand sanitizer dispenser 1103 conveniently available. The wearable hand sanitizer dispenser 1103 can sense a dispenser activation via switch 1115 and transmit this information by way of an RF transmitter located on printed circuit board 1111 held within housing portions 1113a, 1113b. RF signal 1101 is received by logic board 1107 having an RF receiver. Thus handwash activity can be performed conveniently by the user and the activity can be logged.

FIGS. 12A and 12B illustrate a perspective view and a break-away perspective view respectively, of another embodiment of a wearable smart zone center similar to that of FIGS. 10 and 11, but in this case the wearable dispenser 1203 is attached to the lanyard 1003. This embodiment has the advantages of not requiring a clip in order to wear the wearable dispenser and of avoiding the costs and complexity of an RF transmitter circuit and receiver, using instead a wire connection 1201 running through lanyard 1003 and terminating at end region 1205 with a dispensing sensor 1207.

As an example of construction details, the wearable unit in this system can be constructed using a PIC18LF2550 microcontroller, a 24LC256 EEPROM for data storage, a DS1338 real time clock, communicating with microcontroller via I2C interface, and a PNA4602 infrared detector. The short-range RF link between the wireless wearable gel dispenser and the wearable zone sensor can use an rfRXD0420 or MICRF211 based 433.92 MHz receiver.

The wearable electronic units and gel dispensers work in pairs with each dispenser being equipped with a MAX1472 based transmitter to inform corresponding electronic unit about dispenser activations. In this configuration the main functions of wearable electronic unit are to demodulate and decode zone identity signals, record the real time of entering/leaving the zones and dispenser activations, provide prompting if required, store hand hygiene activity history as well as the detected codes of the zones. The hand disinfection status "flags" of the caregiver (clean or dirty) are stored in the wearable unit so it knows whether it has been recently used to disinfect the wearer's hands (this time interval can be set in the software), or whether the wearer's hands have been disinfected since the previous patient zone was visited. Advantageously, this distributed system does not require a real-time central co-coordinator. The data recorded by the wearable smart zone sensors units can be later downloaded to a PC via a USB interface for monitoring and further analysis.

Furthermore, an indication such as a light or other signal unit may be provided integrally the wearable dispenser 1203a as shown in FIG. 12A, for example on the housing 1203, or elsewhere on housing 1113 in FIG. 12B, or separate therefrom, or with the lanyard 1003, or the badge shown at 1013, as an indication of the status flag. This would permit, for instance, a patient in a patient zone to determine if the attending user has executed the required disinfection step before visiting the patient's zone in particular. If the status signal is "red" for instance, it may give the patient a cue to remind the user to disinfect before proceeding further. Alternatively, the patient may see a green signal indicating that the user has indeed disinfected prior to the visit.

Figure 13A:
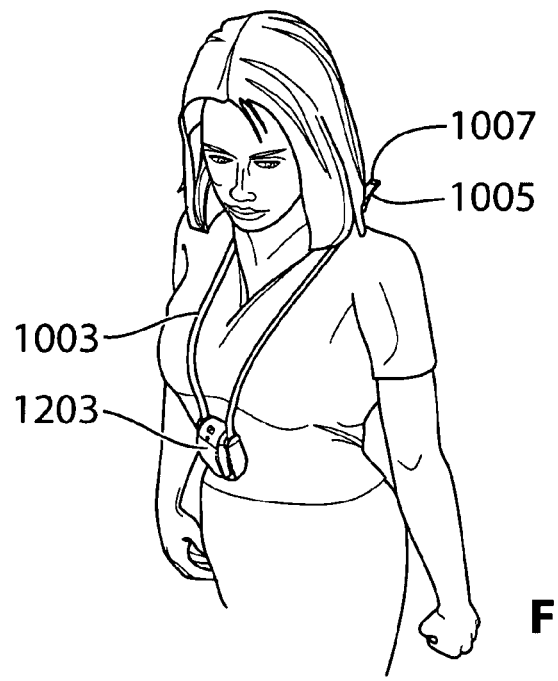
FIGS. 13A, 13B, 13C illustrate various locations for wearing an embodiment of a wearable smart handwash dispenser.
Figure 13B:
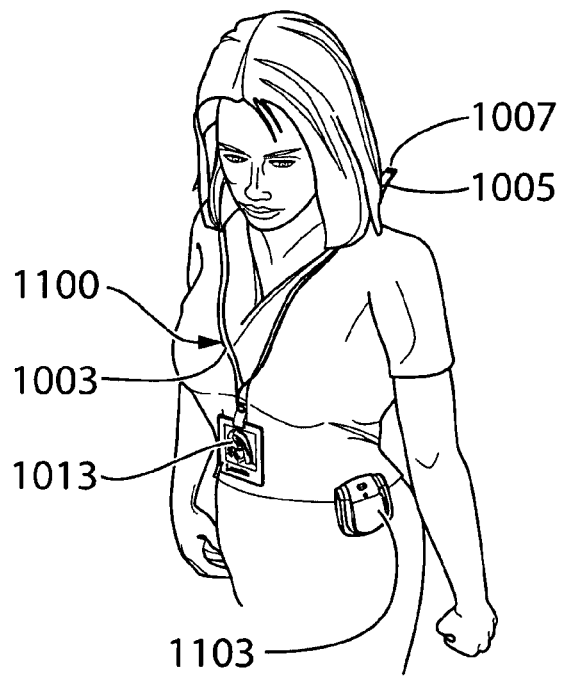
Figure 13C:
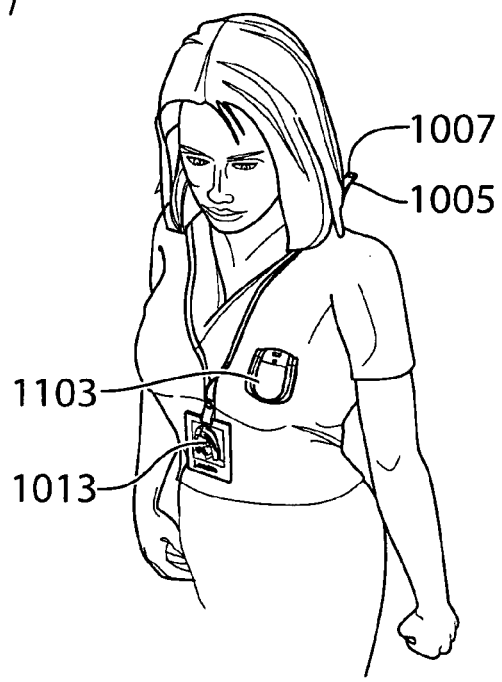

FIGS. 13A, 13B, 13C illustrate various locations for wearing the embodiments of FIGS. 10, 11, 12. Note that infrared sensor 1007 on arm 1005 is exposed beyond the user's hair so as to have improved line-of-sight to at least one infrared transmitter when the user is inside a zone.

Figure 14:
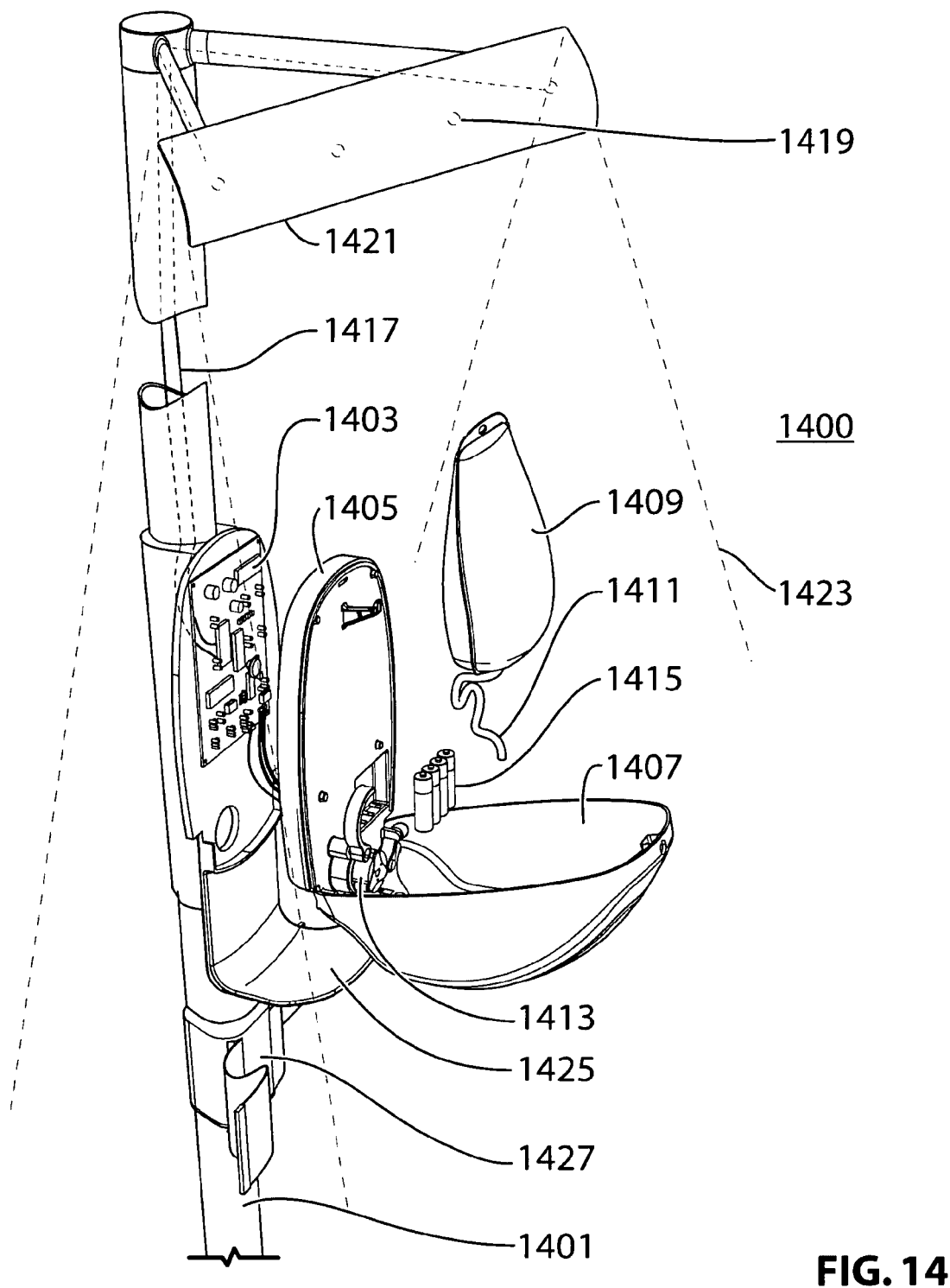
FIG. 14 illustrates a break-away perspective view of a fixed dispenser embodiment of the present invention.

FIG. 14 illustrates a break-away perspective view of an exemplary embodiment of a fixed pylon-mounted dispenser 1400 of the present invention. The fixed dispenser is mounted on pylon or pole 1401. Printed circuit board 1403 comprises controller functions for encoding infrared zone identifier signals, for controlling and interfacing with proximity sensor (not shown), and for controlling a pump such as a peristaltic dispenser pump assembly 1413. The fixed dispenser 1400 uses replaceable refill bag 1409 for providing the disinfecting gel held within housing portions 1405, 1407. The housing portions 1405, 1407 are, in turn, mounted on the pole 1401 with a drip catch tray 1425 located below the outlet of tubing 1411. Tubing 1411 dispenses the disinfecting gel from bag 1409 by squeezing action of rollers of peristaltic pump assembly 1413. The fixed dispenser 1400 uses electric power provided by four AA batteries 1415, or an alternative power supply may be used as desired. In operation when a user places his/her hands under the fixed dispenser 1400 the proximity sensor detects the placement of the hands and the printed circuit board (PCB) control circuit activates the dispensing pump assembly 1413 to dispense sanitizing gel. The dispensing pump assembly 1413 can be programmed to dispense different amounts of gel, for example 1 ml of gel every second for up to four seconds. When a dispensing activation takes place, the PCB control circuit then generates a zone ID signal which travels through wires 1417 to IR emitter array as shown by dashed lines at 1419 behind reflector 1421. This zone ID signal is only transmitted for a short time and is coded to inform the user's wearable smart zone sensor that a hand sanitizing operation has been performed. The logic of the controller of the wearable smart zone sensor will sense the zone ID signal and when it decodes the zone ID as representing the dispensing action, it will set the status flag to "clean" and log the action in the memory. Thus the fixed dispenser creates a "micro zone" where the zone ID signal is transmitted only briefly, following a dispensing action. The zone boundaries 1423 are determined by the shape of reflector 1421.

FIG. 15A illustrates a perspective view of a pylon-mounted fixed dispenser of the present invention. The pylons 1401 are set in bases 1429 to support the pylons. Retractable physical barrier ribbon 1427 can span between pylons or between a pylon and a wall to control pedestrian traffic, and can be used to direct persons to a conveniently located fixed a dispenser to encourage hand hygiene. This can be reinforced by appropriate signs. This arrangement can be useful for controlling hand hygiene compliance in wide hallways, for example, or to define and set up temporary zones.

FIG. 15B illustrates a perspective view of a wall-mounted fixed dispenser 1501 which is similar to the pylon-mounted fixed a dispenser except that it is configured to be mounted on a wall 1500.

Figure 16:
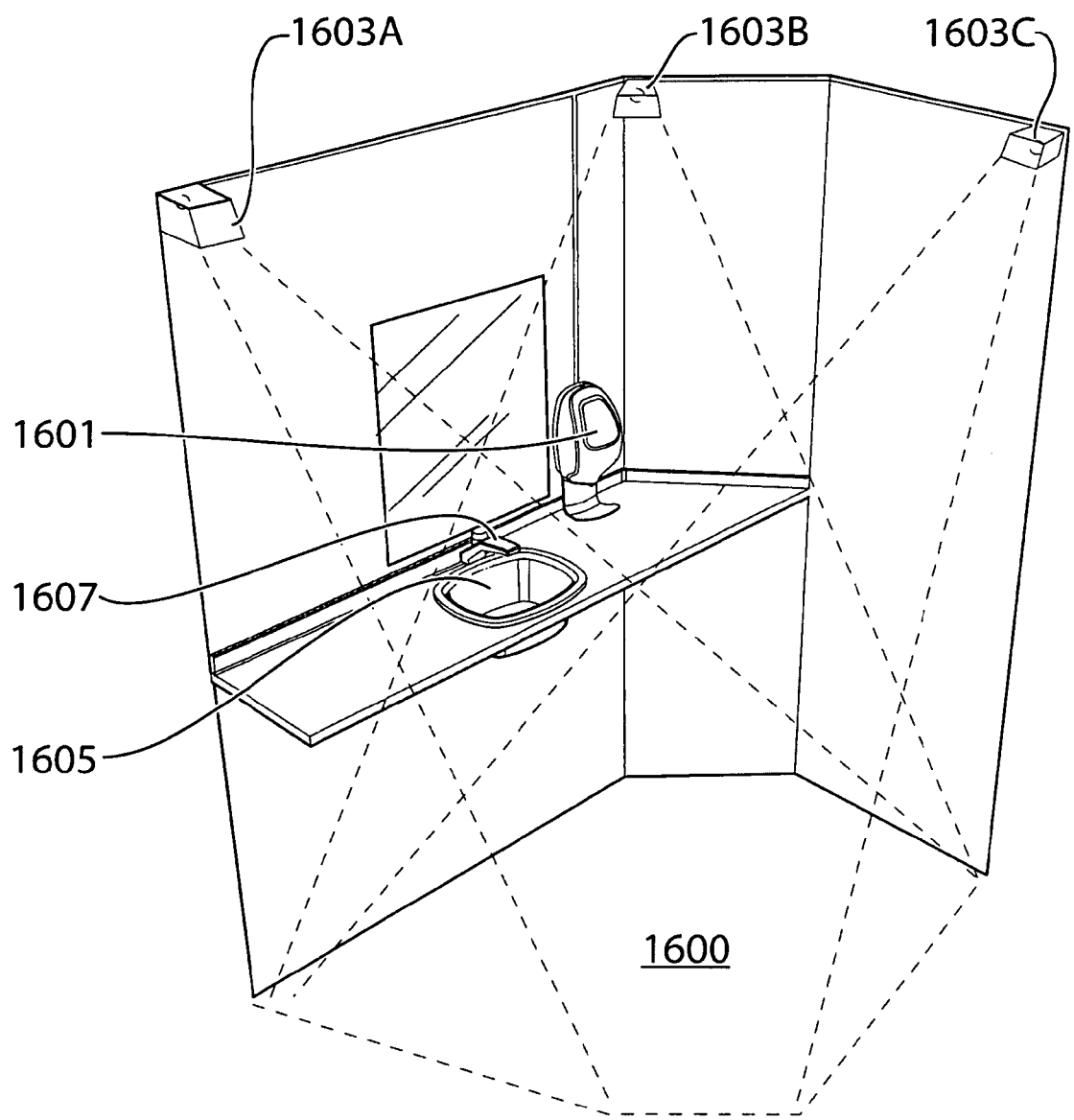
FIG. 16 illustrates a perspective view of a bathroom zone embodiment of the present invention.

FIG. 16 illustrates a perspective view of a bathroom zone embodiment 1600 of the present invention. In this embodiment, fixed dispenser 1601 can be used to dispense liquid soap which can be used in conjunction with water from faucet 1607 and sink 1605. The fixed dispenser 1601 is physically similar to wall-mounted fixed dispenser 1501. Infrared emitters 1603A, 1603B, 1603C transmit a zone identifier signal which is encoded to provide identification of the zone type. Thus when a user wearing a wearable smart zones sensor enters the bathroom zone the smart zone sensor logs the zone identifier for the bathroom zone. Fixed dispenser 1601 is configured to transmit a modified zone identifier signal for a short duration upon dispenser activation. This modified zone identifier signal is encoded to inform the smart zone sensor that a dispenser activation has occurred to allow the smart zone sensor to set the status flag to "clean" and to log the activation in memory. When the user leaves the bathroom zone without a dispenser activation of either the fixed soap dispenser 1601 or a wearable disinfectant dispenser, the smart zone sensor will alert the user with a single long duration prompt. This is a contrasted by the persistent prompt that the user receives from the smart zone sensor when the user enters a patient zone without proper hand cleansing activity. In other embodiments the fixed bathroom zone dispenser 1601 can be applied with disinfecting gel instead of liquid soap. Other embodiments would provide dispensers for liquid soap and for disinfecting gel.

FIG. 17 illustrates a break-away perspective view of an embodiment of a zone controller 1700 of the present invention. The zone controllers 1700 comprise a zone controller housing top 1701 and a printed circuit board controller 1703. The controller is configured to transmit a zone identifier signal to infrared LED emitters 1709 via wires 1707. Each infrared emitter is mounted in a collimator cone 1711 which has a dust cover 1713. In one embodiment the collimators are configured to mount on T-bars of suspended ceilings by means of T-bar clip 1715. Other mounting arrangements for the light-weight collimator cones will be readily apparent to persons skilled in the art. In one embodiment the infrared emitters 1709 are connected in series in groups of six emitters, driven by the current source on printed circuit board controller 1703. Ambient light sensor 1705 is used by controller 1703 to adjust the drive current to the infrared emitters 1709 in order to provide crisp boundaries of the infrared zone, according to varying levels of ambient lighting in the zone.

An entrance zone can be provided using zone controller 1700, configured to transmit a zone identifier signal comprising a zone type identifier. An entrance zone can have different hand hygiene compliance requirements compared to a bathroom zone or a patient zone. The wearable smart zone sensors can be programmed to recognize different zone types by decoding the zone type identifier within the zone identifier signal. Different actions can be taken and different timing parameters can be used by the wearable smart zones sensors responsive to the zone type. For example when the wearable smart zones sensor detects an entrance zone, it can be programmed to produce a single long prompt if cleansing was not performed within the expiring time before entering the zone. When the user leaves the entrance zone and no other zone is detected within a predefined or programmable time. A long prompt is issued. The wearable smart zone sensor can be programmed not to prompt the user as long as the user remains within the entrance zone. The wearable smart zone sensor can also be programmed not to prompt the user when passing through the entrance zone while traveling between patients if proper hygiene procedures were performed between the patient zones.

Figure 18A:
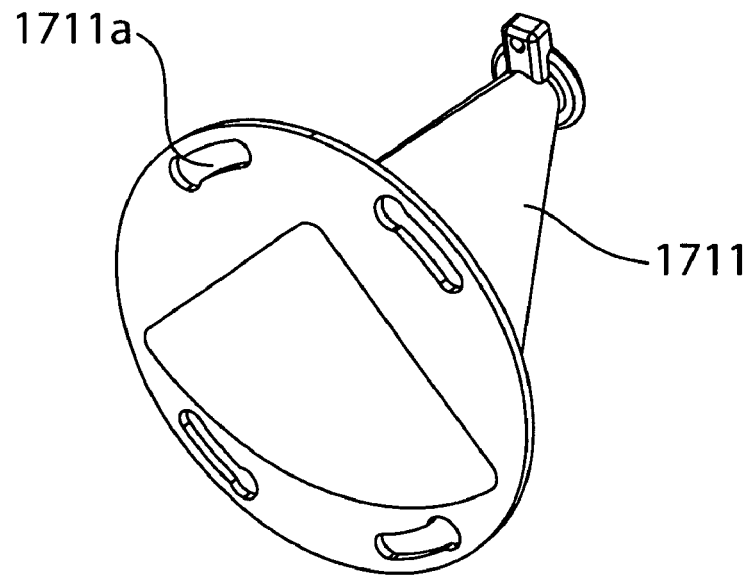
FIG. 18A illustrates a perspective view of an embodiment of a collimator of the present invention.
Figure 18B:
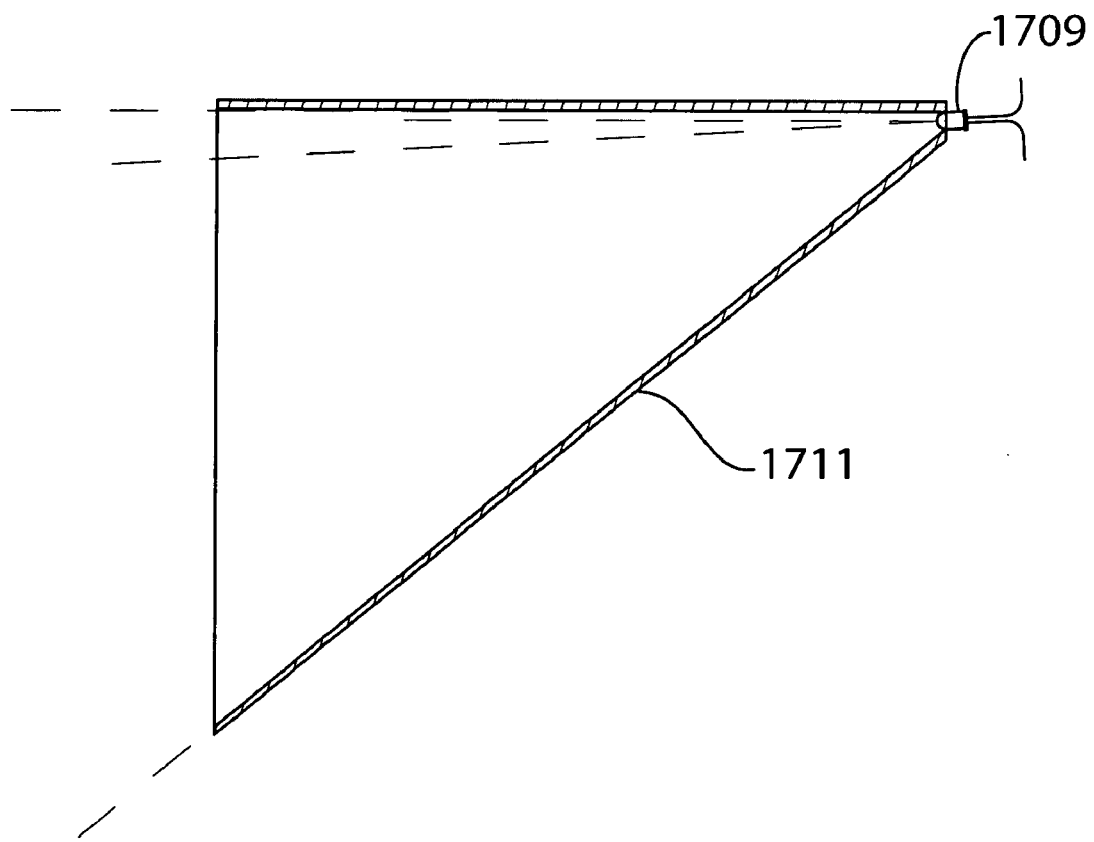
FIG. 18B illustrates a cross-sectional view of the collimator of FIG. 18A.

An embodiment of a collimator 1711 of the present invention is illustrated in FIG. 18A along with a corresponding cross-sectional view in FIG. 18B. The collimator walls restrict the field of emission of the infrared LED as well as providing controlled scattering of the infrared emissions in order to provide even infrared light distribution across the field of emission. The collimator 1711 is provided with keyhole slots 1711a to engage complementary pins, not shown, in the dust cover 1713.

Figure 19:
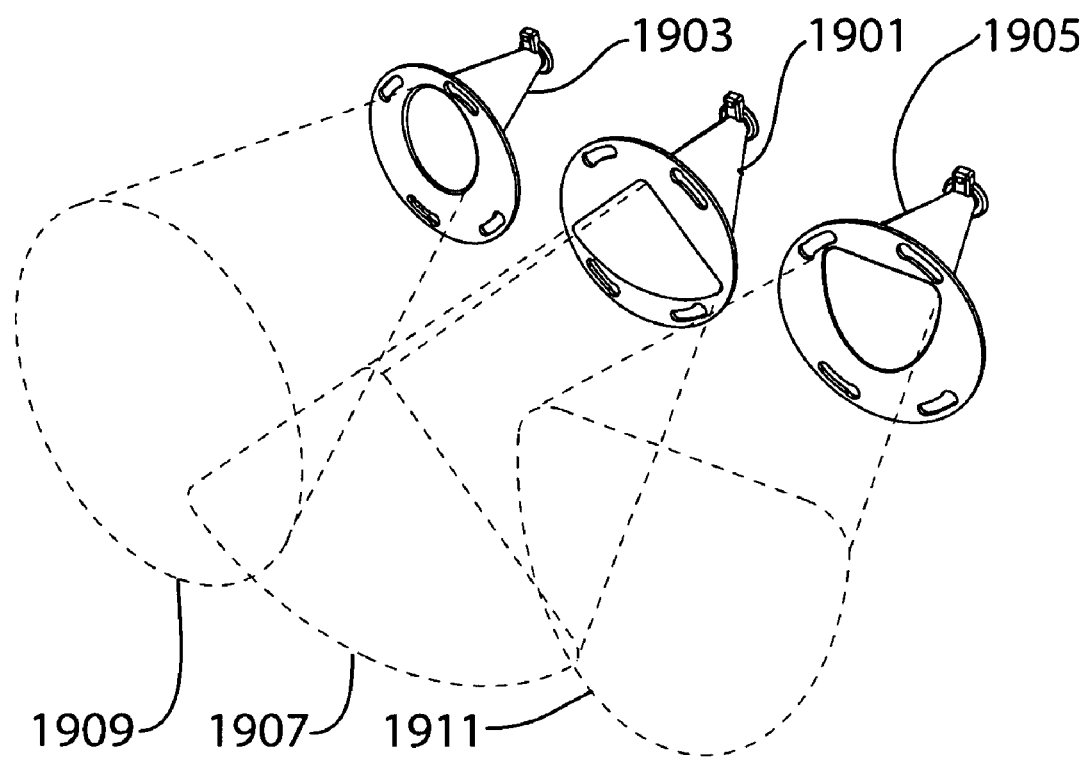
FIG. 19 illustrates exemplary embodiments of various shapes of collimators and the resulting IR emission patterns.
Figure 20:
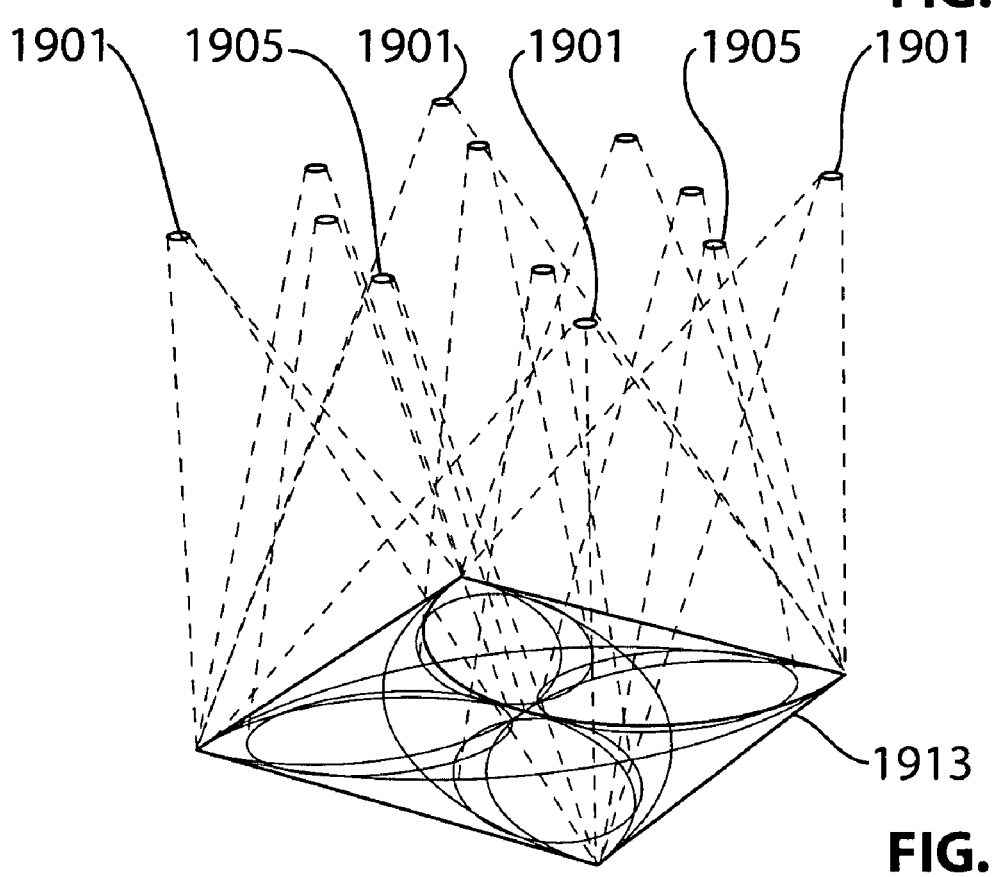
FIG. 20 illustrates an exemplary array of collimators and the resulting cubic zone they define.

FIG. 19 illustrates exemplary embodiments of various shapes of collimators and the resulting IR emission patterns. Thus, collimator 1903 provides a generally circular emission pattern 1909, collimator 1901 provides a generally fan-shaped emission pattern 1907, and collimator 1905 provides a generally semicircular emission pattern 1911. These collimator cones can be combined into an array mounted on a ceiling, to define a cube-shaped zone 1913 for example with well-defined boundaries as shown in FIG. 20. Other shapes of zones having well-defined boundaries can be defined by using different arrays of collimator cones. Well defined boundaries are advantageous when adjacent zones are in close proximity such as for example and adjacent patient beds in a hospital ward.

Figure 21:
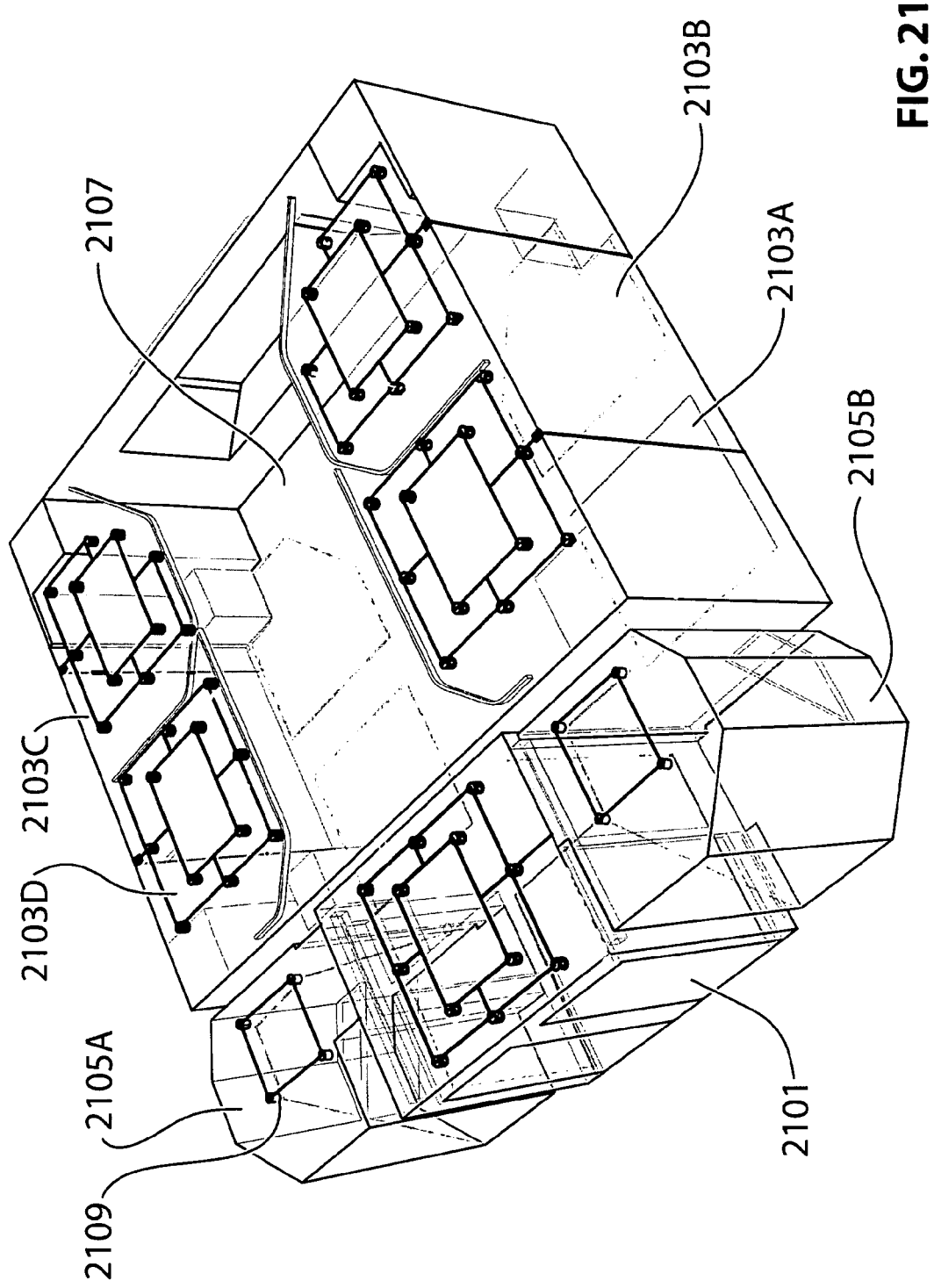
FIG. 21 is a perspective view of an area of an exemplary health care facility illustrating various zone types.

FIG. 21 is a perspective view of an area of an exemplary health care facility illustrating various zone types. In this example and entrance zone 2101 is defined at the entrance of a hospital ward. Patient zones 2103 are defined around patient beds. Bathroom zones 2105 can also be provided.

In some embodiments, zones include an array of 12 I.R. emitters housed in specially designed white plastic Collimators. The geometry of the Collimators is driven by the desired zone boundary, the distance from the floor and their respective location in the array. In a square 12 emitter array, three shapes were determined to be sufficient to provide a cubic zone of detection with a granularity of 5-10 cm. Most zone shapes can be defined by using the three shapes but accommodating a complex custom zone boundary might require custom collimators. While the IR emitters provide effective zone boundaries or delineations, there may be other configurations that enable similar zone boundaries. For example, modules may be available which are one or two dimensional, that is are capable of emitting a signal around or over an area or along a line and which are capable of drawing patterns or lines using visible red semiconductor lasers, such as those which are used in virtual keyboards and laser levels.

Further features may be provided as presented in the following clauses:

A method of encouraging compliance of hand hygiene in a system having a disinfectant dispenser, a dispensing detector, a wearable zone sensor, a controller, a timer means and an alerting means, the method comprising steps of:
  detecting a change of zone of the wearable zone sensor;
  responsive to detecting a change of zone, starting a preset first timer; and
  responsive to expiration of the first timer, activating the alerting means.

A method as defined, further comprising a step of disabling the first timer responsive to sensing dispensing of disinfectant.

A method as defined, wherein the step of detecting a change of zone further comprises steps of:
  sensing a zone identifier signal;
  decoding a first zone identifier from the zone identifier signal;
  comparing the first zone identifier with a stored zone identifier;
  determining a change of zone if said first zone identifier differs from said stored zone identifier; and
  storing said first zone identifier as the stored zone identifier.

A method as defined, further comprising a step of logging the time associated with detecting a change of zone.

A method as defined, further comprising a step of logging the time associated with activating the alerting means.

A method as defined, further comprising a step of logging said first zone identifier associated with detecting a change of zone.

A method as defined, further comprising a step of transmitting said zone identifier signal from a zone transmitter.

A method as defined, wherein said step of transmitting comprises transmitting an ultrasonic signal.

A method as defined, wherein said step of transmitting comprises transmitting a radio frequency signal.

A method as defined, wherein said step of transmitting comprises transmitting an infrared signal.

A method as defined, wherein said step of transmitting comprises transmitting an infrared signal from an array of one or more infrared emitters.

A method as defined, wherein said step of transmitting comprises transmitting said infrared signal within a zone defined by a radiation pattern of each of said infrared emitters.

A method as defined, wherein said disinfectant dispenser is integrated with said wearable zone detector, the method further comprising sensing dispensing of disinfectant by way of a contact closure.

A method as defined, wherein the disinfectant dispenser is separate from the wearable zone detector, the method further comprising steps of at said disinfectant dispenser, transmitting an indication of dispensing of disinfectant to said wearable zone detector, and at said wearable zone detector, receiving said indication of dispensing.

A method as defined, wherein said transmitting said indication of dispensing of disinfectant is performed wirelessly.

A method as defined, wherein the wireless transmitting of said indication of dispensing of disinfectant, uses radio frequency or infrared radiation.

A method as defined, wherein said receiving of said indication of dispensing, is performed by the infrared sensor of said zone sensor.

A method as defined, wherein the indication of dispensing is an infrared signal distinguishable from said zone identifier signals.

A system for encouraging compliance of hand hygiene, the system comprising:
  a disinfectant dispenser;
  a dispensing detector configured to detect operation of said disinfectant dispenser;
  a controller in communication with said dispensing detector;
  a wearable zone sensor in communication with said controller;
  an alerting device in communication with said controller; and
  a zone identification transmitter configured to transmit a zone identification capable of detection by said zone sensor when said zone sensor is within a predefined proximity to said zone identification transmitter,
  wherein said system is configured to activate said alerting means responsive to said dispensing detector not sensing operation of said disinfectant dispenser within a first predefined time delay of said wearable zone sensor detecting a change of zone.

A system as defined, wherein said system is configured to disable said alerting device responsive to said dispensing detector sensing operation of said disinfectant dispenser.

A system as defined, wherein said disinfectant dispenser is integral with said wearable zone sensor.

A system as defined, wherein said disinfectant dispenser is separate from said wearable zone sensor.

A system as defined, wherein said disinfectant dispenser is mounted in a substantially fixed location and said dispensing detector is configured to transmit indication of operation of said disinfectant dispenser, wirelessly to said controller.

A system as defined, further comprising a data memory in communication with said controller, wherein said controller is configured to log into said data memory, a zone identifier for a current zone associated with said change of zone.

A system as defined, wherein said controller is configured to log into said data memory, a zone-change time associated with said change of zone, responsive to said change of zone.

A system as defined, wherein said controller is configured to log into said data memory, a disinfectant dispenser operation time, responsive to sensing operation of said disinfectant dispenser.

A system as defined, further comprising a plurality of zone identification transmitters, each configured to transmit a unique zone identification.

A system as defined, wherein said zone identification transmitter is configured to communicate with said wearable zone sensor via a wireless signal.

A system as defined, wherein said wireless signal is an infrared signal.

A system as defined, wherein each said zone identification transmitter comprises an array of one or more infrared emitters.

A system as defined, wherein each said infrared emitter is configured to emit radiation in a predefined zone.

A system as defined, wherein said predefined zone is determined by a shield having a predefined shape.

A system as defined, wherein said predefined shape is conical.

A system as defined, wherein said predefined shape is a fraction of a cone.

A system as defined, wherein said wireless signal is an ultrasonic signal.

A system as defined, wherein said wireless signal is a radio frequency signal.

A system as defined, further comprising a communication interface configured to interface with a central computer to permit transfer of said logged information from said data memory to said central computer, and wherein said central computer is configured to process said downloaded data to provide indications of hand hygiene compliance.

A system as defined, further comprising a docking station comprising a plurality of said communication interfaces configured to accommodate a plurality of wearable zone sensors.

A system as defined, wherein said system is configured to permit anonymous check out and check in of said wearable zone sensors, wherein each said wearable zone sensor comprises a unique identifier.

A system as defined, wherein said processed downloaded data is retrievable anonymously using said unique zone sensor identifier.

As system as defined, wherein said processed data for a predefined group of zone sensors is retrievable collectively.

A system as defined, wherein said system is configured to permit check out and check in of said wearable zone sensors using a user identifier and wherein said system logs said user identifier.

A system as defined, wherein said system logs said user identifier in said data memory.

A system as defined, wherein said first predefined time delay is a function of zone type as determined from said zone identification.

A system as defined, wherein said zone identification comprises a unique number and wherein said zone identification transmitter is configured to transmit said zone identification as a coded sequence of pulses.

A system as defined, wherein said coded sequence of pulses comprises an integrity check.

A system as defined, wherein said zone identification transmitter is configured to adapt the output level of said transmitted coded pulses responsive to an ambient radiation level.

As system as defined, wherein said alerting device is configured to provide an audible signal.

As system as defined, wherein said alerting device is configured to provide a vibrating signal.

As system as defined, wherein said alerting device is configured to provide a visual signal.

A disinfectant dispenser comprising:
a housing for mounting in a substantially fixed location;
a reservoir for disinfectant agent, supported by said housing;
a dispensing sensor for sensing a dispensing action by a user;
a wireless transmitter configured to transmit an indication of said dispensing action.

A dispenser as defined, wherein said indication is a pulse coded signal.

A dispenser as defined, wherein said pulse coded signal comprises an identifier to identify said dispenser from a plurality of dispensers.

A dispenser as defined, wherein said indication is a radio frequency signal.

A dispenser as defined, wherein said indication is an ultrasonic signal.

A dispenser as defined, wherein said indication is an infrared signal.

A dispenser as defined, wherein said wireless transmitter further comprises an infrared emitter and a shield to control dispersion of infrared radiation.

A zone identification beacon comprising:
an infrared transmitter configured to transmit a zone identification to a defined space,
wherein said zone identification is configured to identify said zone from a plurality of zones, and
wherein said transmitted zone identification is coded as a series of coded pulses.

A zone identification beacon as defined, wherein said infrared transmitter comprises:
a plurality of infrared emitters configured emit an infrared signal corresponding to said zone identification,
wherein said emitters are oriented to cooperate to define an infrared radiation pattern to cover a defined space.

A zone identification beacon as defined, further comprising a plurality of shields to control dispersion of infrared radiation of said infrared emitters.

A zone identification beacon as defined, wherein said zone identification transmitter is configured to adapt the output level of said transmitted coded pulses responsive to an ambient radiation level.

A wearable smart zone sensor configured to be worn by a user, the smart zone sensor comprising:
a zone detector configured to detect a wireless zone identifier signal;
a controller in communication with said zone detector;
a data memory in communication with said controller;
a dispenser activation detector in communication with said controller; and
an alerting device in communication with said controller for alerting the user,
wherein the controller is configured to:
decode a zone identifier from said zone identifier signal;
determine when said smart zone sensor enters a zone responsive to said zone identifier signal and store said zone identifier and time of entering in said data memory;
determine when said smart zone sensor leaves a zone responsive to said zone identifier signal and store said zone identifier and time of leaving in said data memory;
determine when dispenser activation occurs responsive to said dispenser activation detector and store time of dispenser activation in said data memory; and
alert said user when a hand cleansing operation is required.

A wearable smart zone sensor as defined, further comprising an interface for transmitting to an external computer, the data stored in said data memory.

A wearable smart zone sensor as defined, further comprising a housing configured as a user identification card.

A wearable smart zone sensor as defined, further comprising a dispenser for hand cleansing product wherein said dispenser activation detector is configured to detect dispensing of said hand cleaning product.

A wearable smart zone sensor as defined, wherein said dispenser is collocated in said housing with said smart zone sensor.

A wearable smart zone sensor as defined, further comprising a housing for enclosing said smart zone sensor, wherein said housing is configured for attachment to a lanyard.

A wearable smart zone sensor as defined, further comprising an arm pivotally connected to said housing, wherein said arm houses said zone detector and is configured to maintain said zone detector in spaced relationship from said user when said arm is in an operating position and wherein said arm can be pivoted to a storage position.

A wearable smart zone sensor as defined, wherein said zone detector comprises an infrared (IR) sensor.

A wearable smart zone sensor as defined, wherein said dispenser activation detector is configured to receive a wireless signal from a fixed dispenser unit.

A wearable smart zone sensor as defined, wherein said dispenser activation detector is configured to receive an IR signal from said fixed dispenser unit.

A wearable smart zone sensor as defined, wherein said dispenser activation detector is configured to receive a wireless signal from a portable dispenser unit.

A wearable smart zone sensor as defined, wherein said dispenser activation detector is configured to receive a radio frequency (RF) signal from said portable dispenser unit.

A wearable smart zone sensor as defined, wherein said dispenser activation detector is configured for wired communication with a portable dispenser unit, said portable dispenser unit configured for mounting on said lanyard.

A fixed dispenser unit for dispensing a hand cleansing product, said fixed dispenser unit comprising:
a cleansing product container;
a cleansing product dispenser for dispensing said cleansing product from said container;
a wireless zone identifier signal transmitter for transmitting a signal indicative of a dispenser activation and zone identifier for receipt by a smart zone sensor;
a controller for encoding said zone identifier signal.

A fixed dispenser unit as defined, wherein said fixed dispenser unit is configured for mounting on a wall.

A fixed dispenser unit as defined, wherein said fixed dispenser unit is configured for mounting on a pylon.

A fixed dispenser unit as defined, further comprising a proximity sensor for sensing proximity of a user's hands to said dispenser and wherein said controller is further configured to activate said cleansing product dispenser responsive to said proximity sensor sensing a user's hands.

A fixed dispenser unit as defined, wherein said fixed dispenser unit is configured for dispensing a viscous product.

A fixed dispenser unit as defined, wherein said cleansing product dispenser comprises a pump.

A fixed dispenser unit as defined, wherein said wireless zone identifier signal transmitter comprises an infrared emitter.

A wearable sensor for a hand hygiene system, the sensor comprising:
a zone detector configured to detect a wireless zone identifier signal;
a controller in communication with said zone detector;
a data memory in communication with said controller;
a dispenser activation detector in communication with said controller; and
an alerting device in communication with said controller for alerting the user,
wherein the controller is configured to:
decode a zone identifier from said zone identifier signal;
determine when said sensor enters a zone responsive to said zone identifier signal and store said zone identifier and time of entering in said data memory;
determine when said sensor leaves a zone responsive to said zone identifier signal and store said zone identifier and time of leaving in said data memory;
determine when dispenser activation occurs responsive to said dispenser activation detector and store time of dispenser activation in said data memory; and
alert said user when a hand cleansing operation is required.

A wearable sensor as defined, wherein the controller is configured to establish a positive status flag condition indicating a clean hands condition, and a negative status flag condition indicating a dirty hands condition, the positive and negative status flags changing according to one of or more of:
when the smart zone sensor enters a zone;
how long the smart zone sensor remains in a zone;
when the smart zone leaves a zone; and
when the last dispenser activation has occurred.

A wearable sensor as defined, further comprising a status flag signal unit for issuing status flag signals indicative of the positive flag condition and/or the negative status flag condition.

A wearable sensor as defined, the status flag signal unit including an audible and/or visible signal emitter either integrally formed with or separate from the wearable sensor.

A wearable sensor as defined, the signal emitter issuing a green signal indicative of the positive flag condition and a red signal indicative of the negative flag condition.

A wearable sensor as defined, the signal emitter being arranged so that the green and/or red signals are visible to a client of the user.

A wearable sensor as defined, wherein the controller is operable to decode, in addition to the zone identifier, one or more zone type identifiers in the zone identifier signal.

A wearable sensor as defined, the alerting device being operable to issue one or more distinct types of alerts to the user according to the zone type identifier.

A wearable sensor as defined, the one or more zone type identifiers including an identifier that the zone is an isolation region in light of a predetermined communicable disease or condition.

A system as defined, the plurality of zone identification transmitters including a first group of one or more zone identification transmitters which are configured to configured to transmit a unique zone type identification.

A system as defined, each of the zone identifiers in the first group including a switch function to adjust the zone type identification.

A system as defined, the switch function including a switch unit located at the zone identification transmitter.

A system as defined, the switch function being remotely adjusted and/or activated.

A hand hygiene compliance system for a facility comprising a plurality of user-logging units, each to be carried on a user of the facility, the user-logging units operable to communicate with a plurality of dispensers for dispensing disinfectant fluids located within the facility to receive and store signals therefrom indicative of a dispensing event by the user, each user-logging units operable to receive and store location information indicative of a current location of the user-logging unit in the facility, each user-logging unit operable to record at least one time value indicative of at least one predetermined time period during which the user has been at the current location, the user-logging unit being operable to generate a positive status flag when a dispensing event has occurred within the predetermined time period, and a negative status flag when a dispensing event has not occurred within the predetermined time period.

While the present invention has been described for what are presently considered the preferred embodiments, the invention is not so limited. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

The embodiment(s) of the invention described above is (are) intended to be exemplary only. The scope of the invention is therefore intended to be limited solely by the scope of the appended claims.

We claim:

1. A method of monitoring hand hygiene compliance by a user in a facility, that utilizes a wearable zone detector to be worn by the user, the wearable zone detector including an on-board control unit, a data memory, at least one timer, a signal receiver and an alert unit, the method comprising configuring the on-board control unit to:
   a) enable the signal receiver to receive a zone identifier signal from a zone within the facility;
   b) decode a zone identifier from the zone identifier signal to identify the zone by number;
   c) decode a zone type identifier from the zone identifier signal to identify the zone by type;
   d) compare the decoded zone identifier with a stored zone identifier stored in the data memory;
   e) determine a change of zone in response to the decoded zone identifier differing from the stored zone identifier;
   f) responsive to determining a change of zone, adjust the at least one timer according to the decoded zone type identifier;
   g) store the decoded zone identifier as the stored zone identifier;
   h) responsive to determining a change of zone, start the at least one timer;
   i) select one of a number of distinct alerts according to the decoded zone type identifier;
   j) responsive to expiration of the at least one timer, activate the selected alert; and
   l) receive a dispensing event signal from a disinfectant dispenser.

2. A method as defined in claim 1, further comprising configuring the on-board control unit, after 1), to:
   m) disable the at least one timer.

3. A method as defined in claim 2, further comprising configuring the on-board control unit to:
   n) receive the dispensing event signal from a fixed dispenser or a wearable dispenser;
   o) determine a dispenser identifier; and
   p) store the dispenser identifier in the data memory.

4. A method as defined in claim 1, further comprising configuring the on-board control unit to store in the data memory a time associated with determining a change of zone.

5. A method as defined in claim 4, further comprising configuring the control unit to store in the data memory a time associated with activating the selected alert, and to store in the data memory a time associated with receiving the dispensing event signal.

6. A method as defined in claim 3, wherein the wearable dispenser is integrated with the wearable zone detector, the method further comprising issuing the dispensing event signal by way of a contact closure.

7. A method as defined in claim 3, wherein a first dispensing event signal is received from the wearable dispenser using radio frequency and a second dispensing event signal is received from the fixed dispenser using infrared radiation or radio frequency.

8. A method as defined in claim 1, further comprising providing a group of the zone identifier transmitters, each to transmit a zone identifier signal with a zone type identifier representative that the zone is a patient zone, or an isolation region according to a predetermined communicable disease or a predetermined patient condition.

9. A method as defined in claim 8, further comprising configuring each of the zone identifier transmitters to adjust the zone type identifier, according to a change in the communicable disease or condition in the zone.

10. A method as defined in claim 9, further comprising locating a switch function at each zone identifier transmitter for activation by a user for adjusting or activating the zone type identification.

11. A system as defined in claim 10, further comprising providing a remotely accessible switch function for adjusting or activating the zone type identifier.

12. A method as defined in claim 1, further comprising providing a group of the zone identifier transmitters, each to transmit a zone identifier signal with a zone type identifier representative that the zone is a bathroom zone, an entrance zone or a patient zone, and identifying a zone type by decoding the zone type identifier and employing different timing parameters and different alert signals according to the zone type identifier.

13. A method as defined in claim 12, further comprising disabling the at least one timer when the zone type is identified as an entrance zone.

14. A wearable device for encouraging user compliance for hand hygiene among a plurality of users in a facility, the wearable device to be worn by one of the users and comprising: a housing portion; a controller; a data memory for storing data; a wireless receiver for receiving one or more wireless zone signals for identifying predetermined user-accessible zones within the facility; and a dispensing detector for sensing operation of a dispenser; the controller operable to decode the zone signals to identify a zone identifier and a zone type identifier for a corresponding zone; at least one timer responsive to the controller for executing one or more predetermined time sequences according to the zone type; and an alert indicator for issuing one or more alerts to the user from a group of distinct alerts, each of the distinct alerts corresponding to a zone type; the controller operable according to the zone type to select at least one of the predetermined time sequences and at least one of the distinct alerts; the controller being configured to disable the alert indicator responsive to the dispensing detector sensing operation of the dispenser.

15. A device as defined in claim 14, further comprising a housing portion, the dispenser being integrally formed therewith.

16. A device as defined in claim 14, further comprising a housing portion, the dispenser being separate therefrom.

17. A device as defined in claim 14, the controller being configured to determine a change of zone by comparing a current zone identifier with a stored zone identifier.

18. A device as defined in claim 17, the controller being configured to store the current zone identifier in the data memory.

19. A device as defined in claim 18, the controller being configured to store in the data memory, a zone-change time associated with the change of zone, responsive to determining the change of zone.

20. A device as defined in claim 14, the controller being configured to store in the data memory, a dispenser operation time, responsive to sensing operation of the dispenser.

21. A device as defined in claim 14, the controller being programmable to adjust the predetermined time sequences for different clinical environments.

22. A system for encouraging hand hygiene compliance among a plurality of users in a facility of a type having a plurality of user-accessible zones, each zone being identifiable by a zone identifier and being a member of a group of one or more zones of a common type, the system comprising a plurality of zone transmitters, each to be located in a corresponding zone to emit a wireless zone signal with a zone identifier code and a zone type code; a plurality of dispensers, each to be located in or near a corresponding zone or carried by one of the users; and a plurality of wearable detectors, each to be worn by one of the users; each wearable detector including a controller, a data memory for storing data, a wireless receiver for receiving wireless zone signals from a zone transmitter when the user is in or near a corresponding zone, and a dispensing detector for sensing operation of a dispenser; the controller being operable to receive the zone signals to determine a zone identifier for the corresponding zone, and a zone type identifier for the corresponding zone, a timer responsive to the controller for executing one or more predetermined time sequences according to the zone type, and an alert indicator for issuing to the user one or more alerts from a group of distinct alerts; each of the distinct alerts corresponding to a zone type, the controller operable, according to the zone type, to select at least one of the predetermined time sequences and at least one of the distinct alerts; the controller being configured to disable the alert indicator responsive to the dispensing detector sensing operation of the dispenser.

23. A system as defined in claim 22, wherein the dispenser includes a disinfectant dispenser, a soap dispenser and/or a faucet.

24. A system as defined in claim 23, wherein the disinfectant dispenser is integrally formed with the wearable detector.

25. A system as defined in claim 22, wherein the dispenser is mounted in a substantially fixed location and the dispensing detector is configured to wirelessly transmit a dispensing event signal indicative of operation of the disinfectant dispenser.

26. A device as defined in claim 22, the controller being configured to determine a change of zone by comparing a current zone identifier with a stored zone identifier.

27. A system as defined in claim 26, the controller being configured to store the current zone identifier in the data memory.

28. A system as defined in claim 26, the controller being configured to store in the data memory, a zone-change time associated with the change of zone, responsive to the change of zone.

29. A system as defined in claim 28, the controller being configured to store in the data memory, a dispenser operation time, responsive to sensing operation of the dispenser.

30. A system as defined in claim 22, the controller being programmable according to the zone type identifier to adjust the predetermined time sequences for different clinical environments.

* * * * *